(12) United States Patent
Vale et al.

(10) Patent No.: US 11,446,045 B2
(45) Date of Patent: Sep. 20, 2022

(54) DEVICES AND METHODS FOR REMOVAL OF ACUTE BLOCKAGES FROM BLOOD VESSELS

(71) Applicant: Neuravi Limited, Galway (IE)

(72) Inventors: David Vale, Galway (IE); Brendan Casey, Galway (IE); Micheal Gilvarry, Galway (IE); Kevin McArdle, Galway (IE); Maeve Holian, Galway (IE); David Hardiman, Dublin (IE); Alan Keane, Dublin (IE); Daniel King, Galway (IE)

(73) Assignee: Neuravi Limited, Galway (IE)

( * ) Notice: Subject to any disclaimer, the term of this patent is extended or adjusted under 35 U.S.C. 154(b) by 247 days.

(21) Appl. No.: 16/505,808

(22) Filed: Jul. 9, 2019

(65) Prior Publication Data
US 2019/0328411 A1    Oct. 31, 2019

Related U.S. Application Data

(63) Continuation of application No. 14/737,249, filed on Jun. 11, 2015, now Pat. No. 10,441,301.
(Continued)

(51) Int. Cl.
*A61B 17/22* (2006.01)
*A61M 1/00* (2006.01)
(Continued)

(52) U.S. Cl.
CPC ........ *A61B 17/22032* (2013.01); *A61B 17/22* (2013.01); *A61B 17/221* (2013.01);
(Continued)

(58) Field of Classification Search
CPC . A61B 17/22032; A61B 17/22; A61B 17/221; A61B 2017/0078; A61B 2017/22079; A61M 25/0082
See application file for complete search history.

(56) References Cited

U.S. PATENT DOCUMENTS

| 4,243,040 A | 1/1981 | Beecher |
| 4,324,262 A | 4/1982 | Hall |

(Continued)

FOREIGN PATENT DOCUMENTS

| CN | 1658920 A | 8/2005 |
| CN | 1972728 A | 5/2007 |

(Continued)

OTHER PUBLICATIONS

US 6,348,062 B1, 02/2002, Hopkins (withdrawn)
(Continued)

*Primary Examiner* — Alexander J Orkin
(74) *Attorney, Agent, or Firm* — Troutman Pepper Hamilton Sanders LLP

(57) ABSTRACT

A system for assisting in the retrieval of a clot from a vessel. The system can include an outer catheter and an inner catheter disposed in a lumen of the outer catheter. The inner catheter can include a distal end, a proximal end, a distal segment, a proximal segment, and a lumen extending proximal of the distal end and terminating at a transfer port at the proximal end of the distal segment. A seal is located on the outer surface of the inner catheter distal of the transfer port, the seal capable of sealing against the lumen of the outer catheter so that aspiration applied through the outer catheter is configured to be transferred to the inner catheter.

11 Claims, 35 Drawing Sheets

Related U.S. Application Data

(60) Provisional application No. 62/080,724, filed on Nov. 17, 2014, provisional application No. 62/011,934, filed on Jun. 13, 2014.

(51) Int. Cl.
    *A61B 17/221*     (2006.01)
    *A61M 25/00*     (2006.01)
    *A61B 17/34*     (2006.01)
    *A61B 17/00*     (2006.01)

(52) U.S. Cl.
CPC ............... *A61M 1/74* (2021.05); *A61M 1/84* (2021.05); *A61M 25/0082* (2013.01); *A61B 2017/00778* (2013.01); *A61B 2017/2215* (2013.01); *A61B 2017/22051* (2013.01); *A61B 2017/22067* (2013.01); *A61B 2017/22079* (2013.01); *A61B 2017/3435* (2013.01); *A61M 2210/12* (2013.01)

(56) References Cited

U.S. PATENT DOCUMENTS

| | | |
|---|---|---|
| 4,351,342 A | 9/1982 | Witta et al. |
| 4,575,371 A | 3/1986 | Nordqvist et al. |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |

(56) References Cited

U.S. PATENT DOCUMENTS

| | | |
|---|---|---|
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukemik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Uteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |

(56) References Cited

U.S. PATENT DOCUMENTS

| | | |
|---|---|---|
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,775,706 B2 | 3/2017 | Paterson et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 2001/0003315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1* | 11/2002 | Bagaoisan ............ A61M 25/00 604/6.12 |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1* | 1/2004 | Adams ................ A61B 17/221 606/194 |
| 2004/0010282 A1* | 1/2004 | Kusleika ................ A61F 2/013 606/200 |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2004/0193107 A1 | 9/2004 | Pierpont |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0267491 A1 | 12/2005 | Kellett et al. |
| 2005/0288686 A1 | 12/2005 | Sepetka |
| 2006/0009785 A1 | 1/2006 | Maitland et al. |
| 2006/0009799 A1 | 1/2006 | Kleshinski et al. |
| 2006/0030933 A1 | 2/2006 | DeLeggge et al. |
| 2006/0058836 A1 | 3/2006 | Bose |
| 2006/0058837 A1 | 3/2006 | Bose |

(56) References Cited

U.S. PATENT DOCUMENTS

| | | |
|---|---|---|
| 2006/0058838 A1 | 3/2006 | Bose |
| 2006/0064151 A1 | 3/2006 | Guterman et al. |
| 2006/0106361 A1 | 5/2006 | Muni |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslayski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin |
| 2011/0213297 A1 | 9/2011 | Klog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera |
| 2012/0041449 A1 | 2/2012 | Eckhouse et al. |
| 2012/0041474 A1 | 2/2012 | Eckhouse et al. |
| 2012/0059356 A1 | 3/2012 | diPalma et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |

(56) References Cited

U.S. PATENT DOCUMENTS

| | | |
|---|---|---|
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0297252 A1 | 10/2015 | Miloslayski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0042623 A1 | 2/2018 | Batiste |
| 2018/0193591 A1 | 7/2018 | Jaroch et al. |
| 2018/0235743 A1 | 8/2018 | Farago et al. |
| 2019/0021755 A1 | 1/2019 | Johnson et al. |

(56) References Cited

U.S. PATENT DOCUMENTS

| | | |
|---|---|---|
| 2019/0021759 A1 | 1/2019 | Krolik et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0255290 A1 | 8/2019 | Snyder et al. |
| 2019/0365411 A1 | 12/2019 | Avneri et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 202009001951 U1 | 4/2010 |
| DE | 102009056450 | 6/2011 |
| DE | 102010010849 | 9/2011 |
| DE | 10 2010 014778 A1 | 10/2011 |
| DE | 102010024085 | 12/2011 |
| DE | 102011014586 B3 | 9/2012 |
| EP | 2301450 B1 | 11/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| GB | 2498349 A | 7/2013 |
| JP | 0919438 A1 | 1/1997 |
| WO | 93/04722 A2 | 3/1993 |
| WO | WO 94/24926 | 11/1994 |
| WO | WO 97/27808 | 8/1997 |
| WO | WO 97/38631 A1 | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 2004/056275 A1 | 7/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | 03/018085 A2 | 3/2003 |
| WO | WO 03/030751 | 4/2003 |
| WO | WO 03/051448 | 6/2003 |
| WO | WO 2004/028571 A2 | 4/2004 |
| WO | WO 2005/000130 A1 | 1/2005 |
| WO | WO 2005/027751 A1 | 3/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | WO 2009/019664 A1 | 2/2009 |
| WO | WO 2009/031338 A1 | 3/2009 |
| WO | WO 2009/076482 | 6/2009 |
| WO | WO 2009/086482 | 7/2009 |
| WO | WO 2009/103125 A1 | 8/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/120490 A2 | 9/2012 |
| WO | WO 2012/110619 A9 | 10/2012 |
| WO | 2012156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 201 4/1 781 9 | 11/2014 |
| WO | WO 2 01 5/061 36 | 4/2015 |
| WO | WO 2015/134625 A1 | 9/2015 |
| WO | WO 2015/179324 A2 | 11/2015 |
| WO | WO 2015/179377 A1 | 11/2015 |
| WO | 2015189354 A1 | 12/2015 |
| WO | WO 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |

OTHER PUBLICATIONS

International Search Report and Written Opinion issued for Application No. PCT/EP2017/0696688 dated Nov. 27, 2017.

International Search Report of PCT/IE2011/000057, dated Feb. 3, 2012 (5 pages).

International Search Report of PCT/IE2012/000011, dated Oct. 10, 2012 (3 pages).

U.S. Office Action issued in corresponding U.S. Appl. No. 15/158,384 dated Jun. 12, 2019.

Written Opinion and International Search Report, dated Jul. 27, 2011, from international Application No. PCT/IE2011/000026 (8 pages).

Office Action issued in U.S. Appl. No. 14/737,249 dated Apr. 10, 2018.

Office Action issued in U.S. Appl. No. 15/158,384 dated Jul. 20, 2018.

Partial European Search Report issued in Application 17204015.6 dated May 17, 2018.

Struffert, T., et al. "Intravenous flat detector CT angiography for non-invasive visualisation of intracranial flow diverter: technical feasibility" Eur Radiol 21:1797-1801 (2011).

Chinese Office Action and Search Report issued corresponding CN Application No. 201711215349.7 dated Feb. 10, 2022.

* cited by examiner

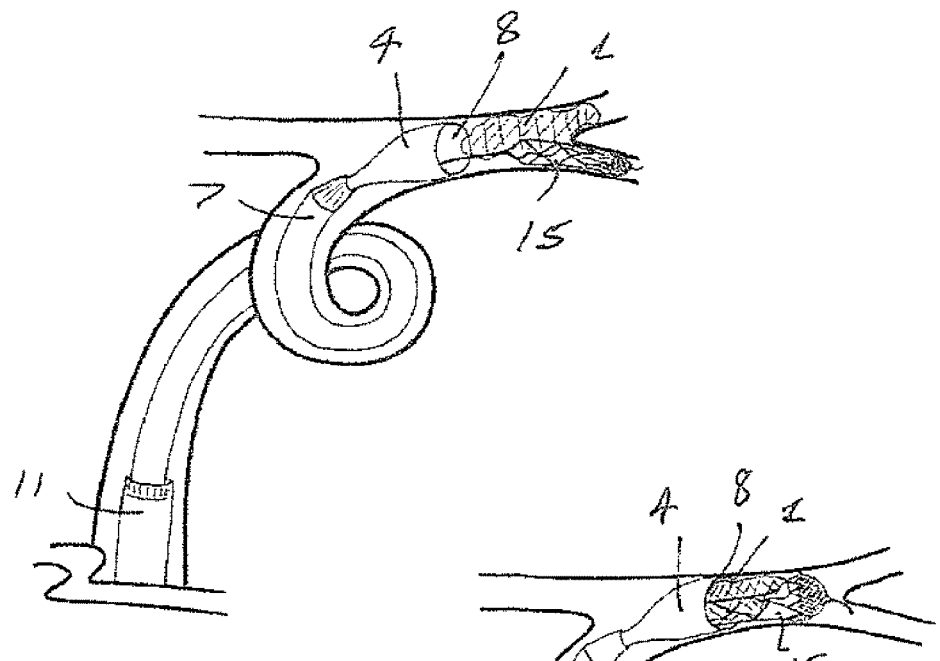
Fig 2d
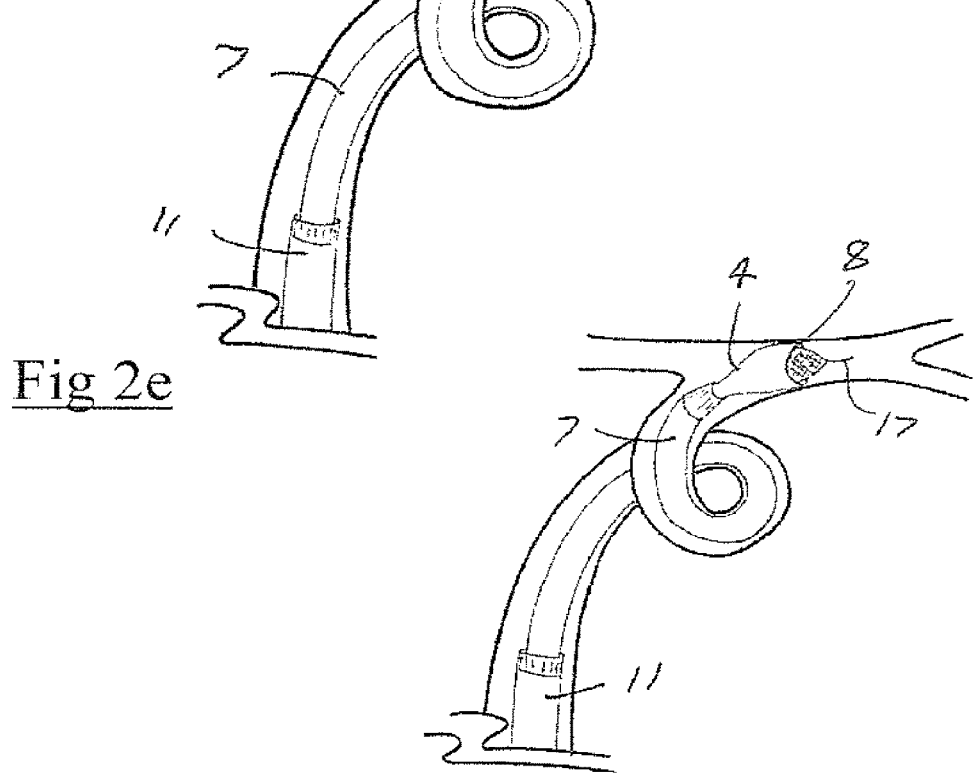
Fig 2e
Fig 2f

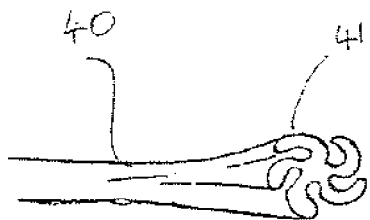 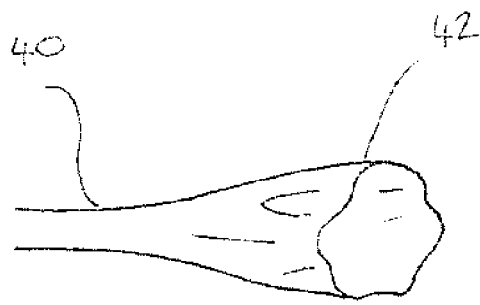
Fig 6a  Fig 6b
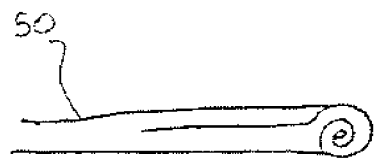 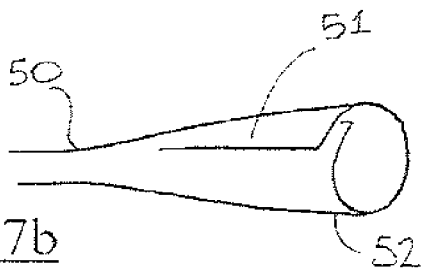
Fig 7a  Fig 7b
 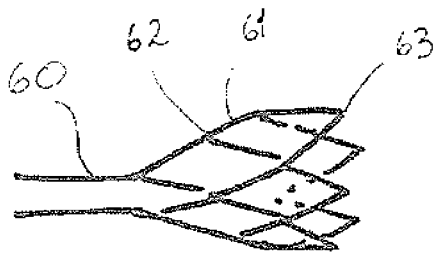
Fig 8a  Fig 8b
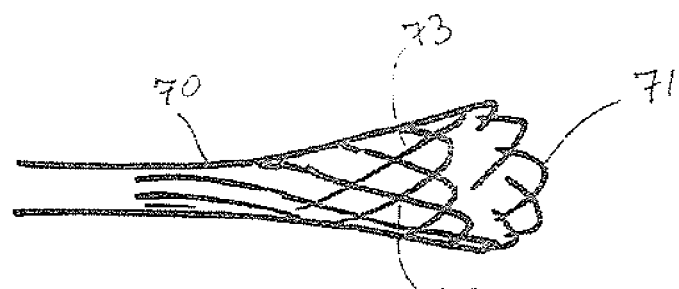
Fig 9

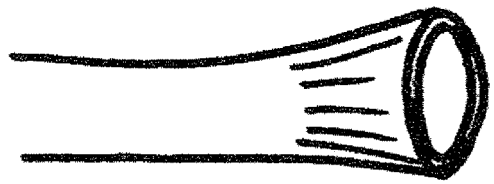
Fig 22a
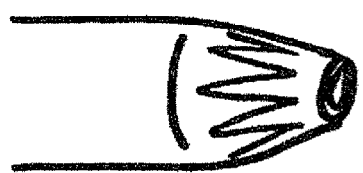
Fig 22b
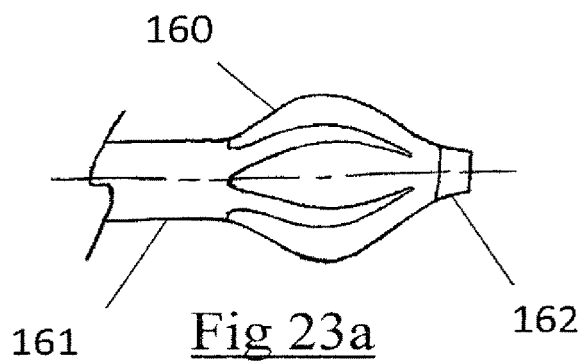
Fig 23a
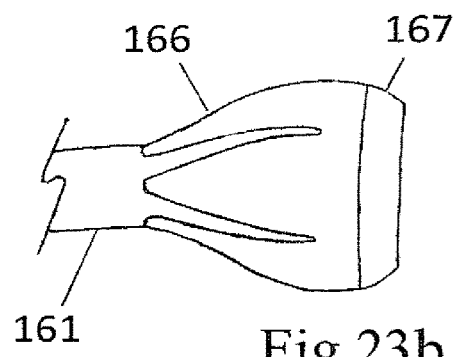
Fig 23b
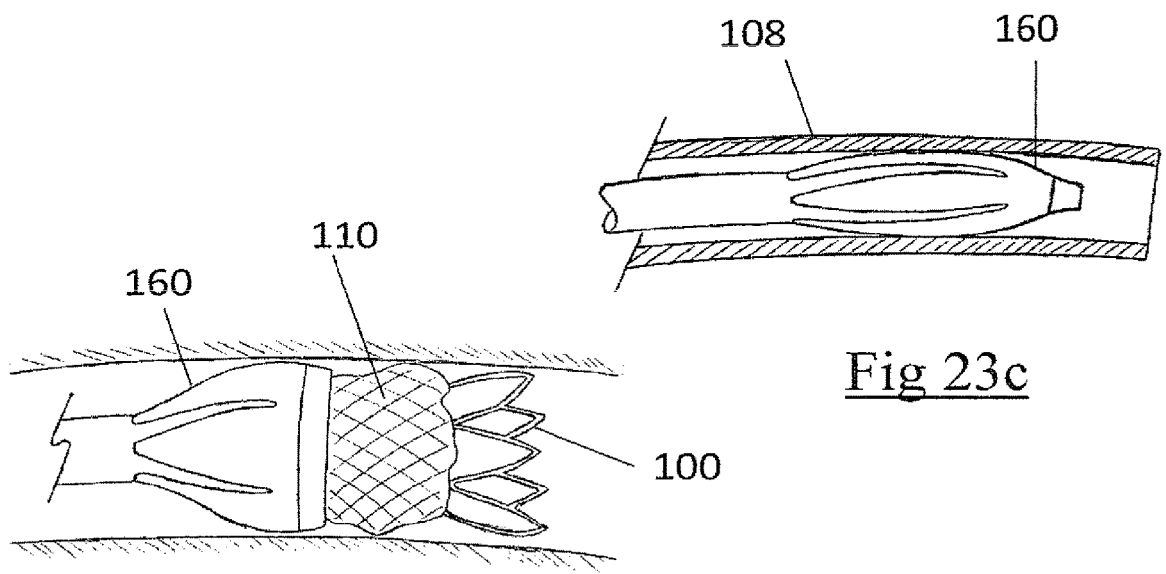
Fig 23c
Fig 23d

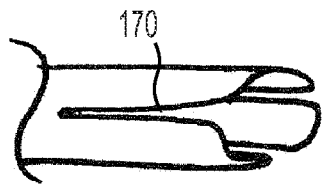
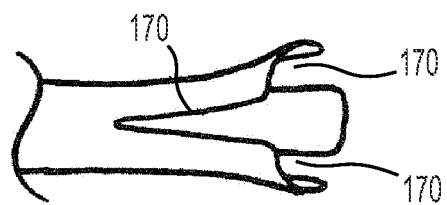
FIG. 29   FIG. 30
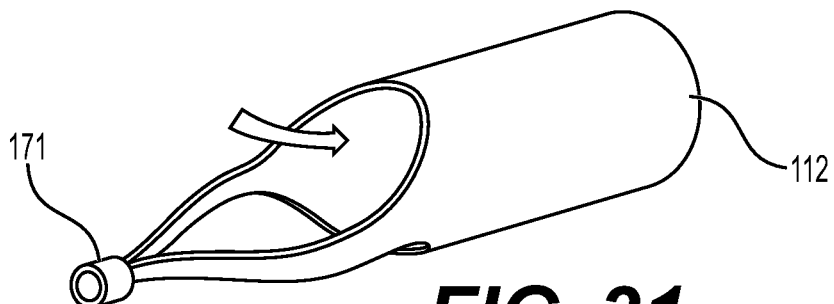
FIG. 31
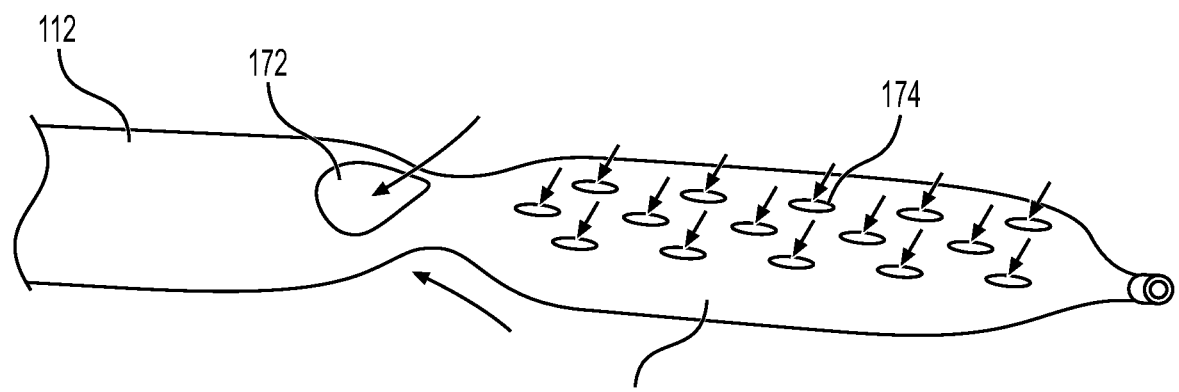
FIG. 32
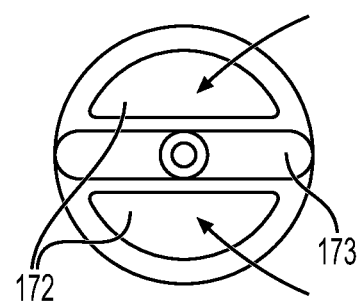
FIG. 33

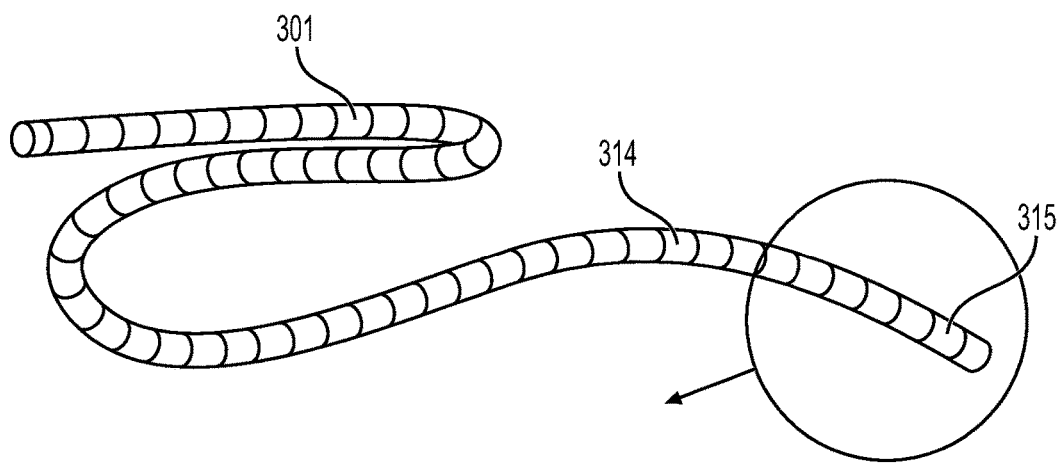
FIG. 44
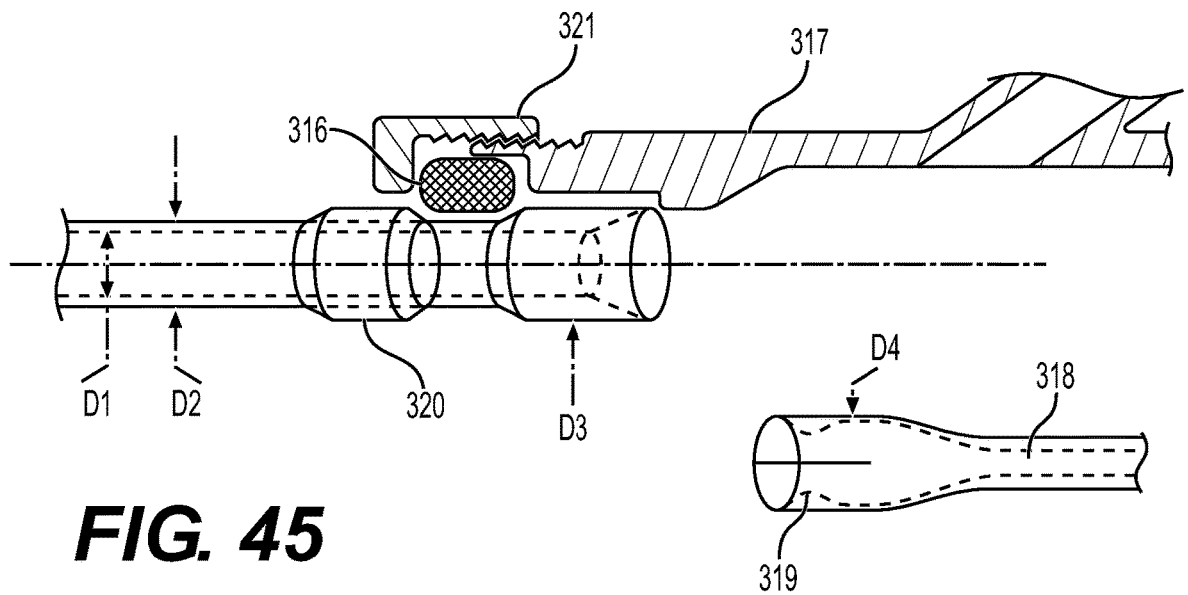
FIG. 45
FIG. 46

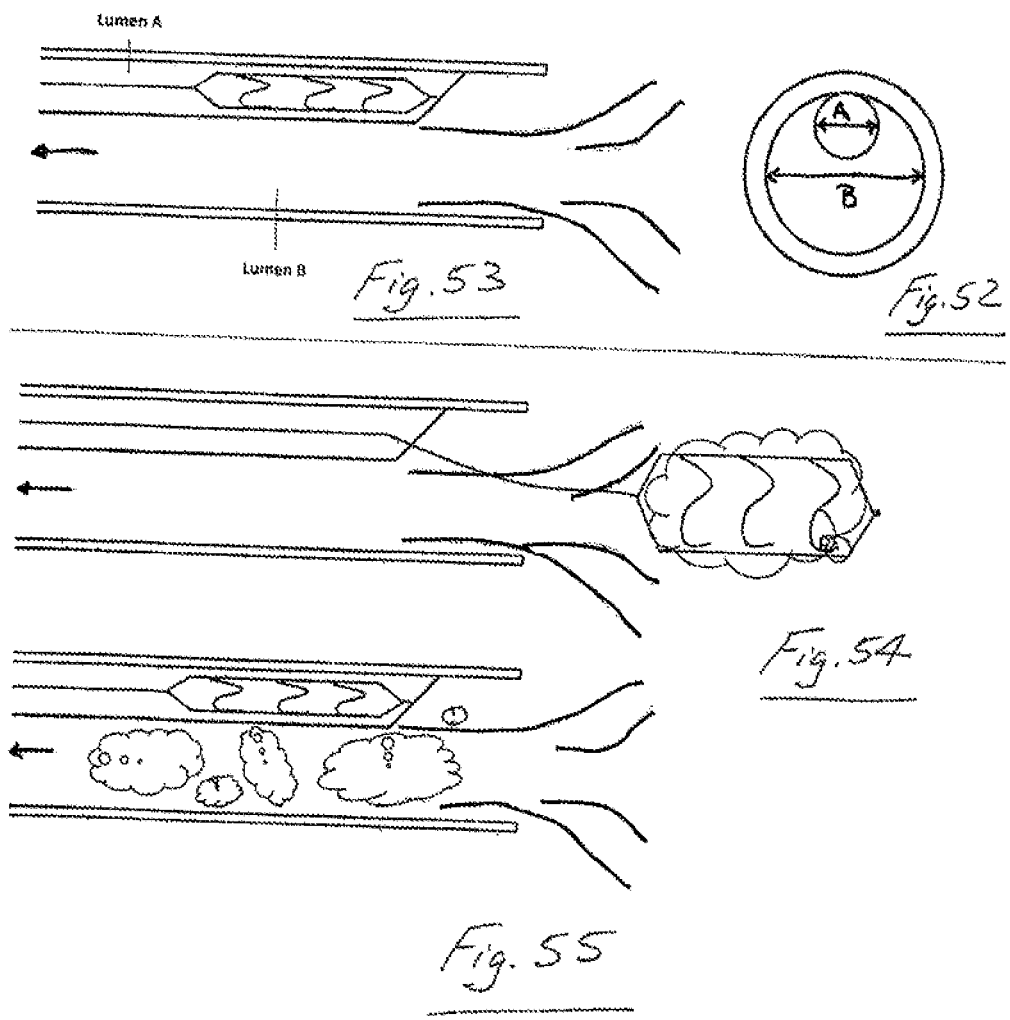

DEVICES AND METHODS FOR REMOVAL OF ACUTE BLOCKAGES FROM BLOOD VESSELS

CROSS REFERENCE TO RELATED APPLICATIONS

This application is a Continuation of U.S. application Ser. No. 14/737,249, filed Jun. 11, 2015 which claims the benefit of U.S. Provisional Application No. 62/011,934 filed Jun. 13, 2014, and U.S. Provisional Application No. 62/080,724 filed Nov. 17, 2014 all of which are incorporated herein by reference in their entirety.

FIELD OF THE INVENTION

This invention relates to devices intended for removing acute blockages from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

SUMMARY OF INVENTION

According to the invention there is provided a catheter for assisting in the retrieval of a clot from a vessel comprising a distal end and a proximal end, a distal segment and a proximal segment and a lumen extending proximal of the distal end and terminating at a transfer port at the proximal end of the distal segment and a flow restrictor located on the outer surface of the catheter distal of the transfer port.

In one case the catheter is an aspiration catheter for aspirating a clot.

In one embodiment the flow restrictor is actuatable between engaged and disengaged configuration. The catheter may comprise an actuator for selectively engaging and/or disengaging the flow restrictor.

In one case the flow restrictor comprises a framework and a membrane coupled to the framework, the framework being movable by the actuator between an expanded configuration and a retracted configuration.

The aspiration catheter may comprise a proximal flow restrictor proximate the proximal end of the distal segment and a distal flow restrictor spaced distally from the proximal flow restrictor.

In one case the distal end of the catheter comprises a mouth for reception of clot. The mouth may be defined by an expansile tip.

In one embodiment the distal segment includes a hinge adjacent to the distal mouth. The hinge may be defined by a region of the distal segment which is configured to have lateral flexibility.

In one case the mouth has an expanded configuration and a retracted configuration. The catheter may comprise a control member for controlling the movement of the mouth between the expanded and retracted configurations.

In one embodiment the mouth comprises a number of segments and the control member is configured to move at least some of the segments. The control member may comprise a draw string or the like.

In another aspect the invention provides a catheter for aspirating a clot in a vessel comprising a distal end and a proximal end, a distal segment and a proximal segment and a lumen extending proximal of the distal end and terminating at a transfer port at the proximal end of the distal segment wherein the distal end of the catheter comprises a mouth for reception of clot. The mouth may be defined by an expansile tip. In one case the catheter has a flow restrictor located on the outer surface of the catheter distal of the transfer port.

Also provided is a system for treating an occlusion in a vessel the system comprising:—a first catheter and a second catheter;

the first catheter comprising a proximal end, a distal end and a lumen extending between the proximal end and the distal end, the lumen of the first catheter further comprising a proximal segment and a distal segment; the second catheter comprising a distal end and a proximal end, a distal segment and a proximal segment, and a lumen, said lumen extending proximal of the distal end and terminating at a transfer port at the proximal end of the distal segment; the first catheter being configured to facilitate aspiration through the lumen; the transfer port being configured to transmit aspiration in the proximal lumen of the first catheter into the lumen of the distal segment of the second catheter and the distal end of the second catheter being configured to receive clot into at least a portion of the lumen of the second catheter.

In one embodiment the system further comprises a flow restrictor between the first catheter and the distal segment of the second catheter, distal of the transfer port. The flow restrictor may be located on the inner surface of the first catheter. Alternatively or additionally the flow restrictor is located on the outer surface of the second catheter.

In one embodiment there is a proximal flow restrictor proximate the proximal end of the distal segment of the second catheter and a distal flow restrictor spaced distally from the proximal flow restrictor.

In one case the distal end of the second catheter comprises a mouth for reception of clot. The mouth may be defined by an expansile tip.

In one embodiment the transfer port comprises a rapid exchange port.

In one case the first catheter is a guide catheter. The second catheter may be an intermediate catheter.

The system may also include a microcatheter which is adapted to be advanced through the first catheter and the second catheter. The system may further comprise a clot engaging device for delivery from the microcatheter.

Also provided is a method of removing a clot from a vessel, the method comprising:—providing a guide catheter and an intermediate catheter, the intermediate catheter having a distal mouth and being configured such that it is advancable within the lumen of the guide catheter; inserting the guide catheter into a first vessel proximal of an occlusion;

advancing the intermediate catheter through the lumen of the guide catheter until the tip of the intermediate catheter extends distal of the guide catheter into a second vessel adjacent to the occlusion; applying aspiration to the proximal end of the guide catheter; the intermediate catheter being configured to direct said aspiration through the distal lumen of the intermediate catheter to aspirate the clot into the mouth of said intermediate catheter.

The aspiration catheter may comprise a distal end, a proximal end, a distal segment, a proximal segment and a lumen extending proximal of the distal end and terminating at a transfer port at the proximal end of the distal segment.

In one embodiment the method comprises restricting flow between the outside surface of the intermediate catheter and the inside surface of the guide catheter.

In one embodiment the method comprises the step, before or after aspiration, of delivering a microcatheter to the occlusion and deploying a clot capture device from the microcatheter. The method may comprise advancing the microcatheter to the clot, deploying a clot capture device from the microcatheter, retracting the microcatheter to a location proximal of a transport port at the proximal end of a distal segment of the aspiration catheter.

In a further aspect the invention provides method of removing an occlusion from a vessel comprising:— providing a first aspiration catheter and a second aspiration catheter, the second aspiration catheter extending distal of the first aspiration catheter and further comprising a transfer lumen proximal of the distal end of the first aspiration catheter; inserting the first catheter into a first vessel proximal of the occlusion; advancing the second catheter through the lumen of the first catheter until the tip of the second catheter extends distal of the first catheter into a second vessel and is substantially opposing the occlusion; and aspirating through the proximal lumen of the first catheter so as to urge the clot into the distal lumen of the second catheter.

The method may comprise restricting flow between the outside surface of the second catheter and the inside surface of the first catheter.

The method may comprise the step, before or after aspiration, of delivering a microcatheter to the occlusion and deploying a clot capture device from the microcatheter. In one case the method as comprises the step, prior to aspiration, of retracting the microcatheter to a location proximal of the transfer port.

In one embodiment the first aspiration catheter is a guide catheter. In one case the second aspiration catheter is an intermediate catheter.

In one aspect the invention provides a clot receptor device. In one case the device is a catheter which may include rapid exchange features. In one embodiment the device provides a self-expanding aspiration catheter with flow-arrest.

The aspiration assist device has a distal end which expands to seal against the vessel proximal of the clot and provides a large open mouth to receive clot easily without risk of dislodging the clot from the thrombectomy device (if used).

The inner rapid exchange expandable device is delivered through an outer catheter, which may be a conventional intermediate or aspiration catheter or a distal access catheter (DAC). In one case it is a tailored catheter with an extremely trackable distal section for ease of access. This outer catheter trackability is possible because the distal section does not require much axial stiffness, as neither clot not thrombectomy device are retracted directly into it.

The rapid exchange (RX) expanding device may be supplied within the outer catheter (about 15 cm proximal of the distal end) and both are delivered together over a microcatheter (or wire) until the outer catheter tip approaches the clot. The inner RX expanding device is advanced to the distal end of the outer, and the outer is then retracted to deploy the self expanding RX device.

The Rx device seals against the vessel wall and against the inner lumen of the outer catheter to allow highly effective aspiration, and its distal end expands to provide a large opening and reception space to receive the target clot and thrombectomy device (if used).

In another similar embodiment the self expanding aspiration catheter has a full length tubular proximal shaft, rather than a rapid exchange shaft, so that it does not require a proximal seal and aspiration can be applied by applying a vacuum force to its proximal hub.

The invention also provides a rapid exchange aspiration catheter.

The catheter provides a proximal seal against guide catheter inner lumen so that aspiration may be applied through the guide taking advantage of the large proximal lumen.

The catheter having deliverability advantages of minimal frictional engagement with guide or microcatheter proximal of exit port.

Retracting the microcatheter just proximal of exit port (rather than completely removing it) creates a large aspiration advantage.

Also provided is a removable microcatheter hub that enables physician to advance a DAC over the microcatheter after the microcatheter (and thrombectomy device) are already in position (as bail, out for example).

BRIEF DESCRIPTION OF THE DRAWINGS

FIGS. 1 and 2a to 2f illustrate a clot receptor device and system according to the invention;
FIGS. 3 to 9 illustrate various alternative clot receptors;
FIGS. 14 to 37b illustrate various alternative distal ends and expansile tips of a clot collector device of the invention;
FIGS. 39 to 46 illustrate a removable microcatheter hub according to the invention;
FIGS. 52 to 55 illustrate a dual lumen aspiration catheter according to the invention.

DETAILED DESCRIPTION OF THE DRAWINGS

Figure 1:
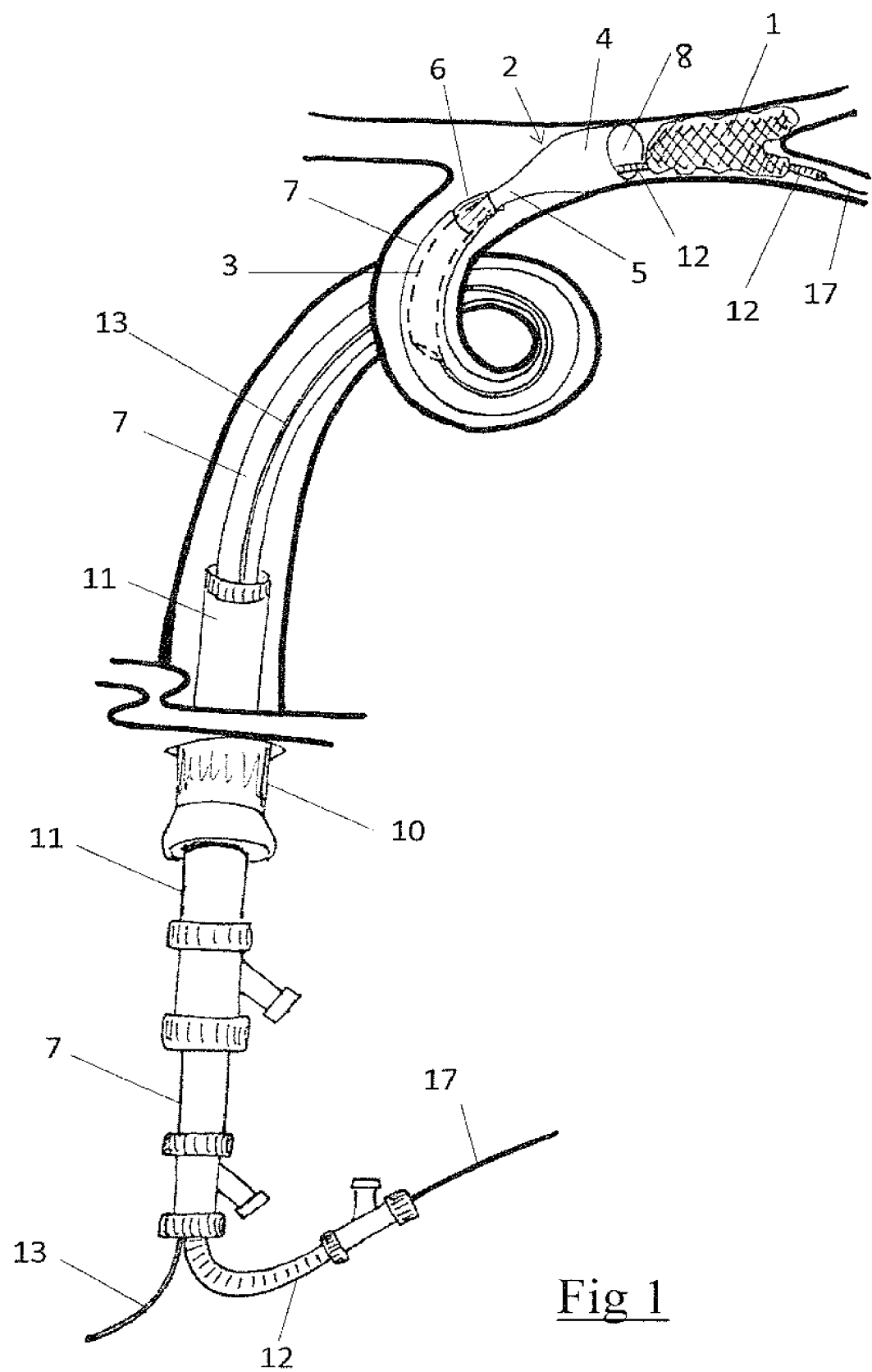
Figure 2A:
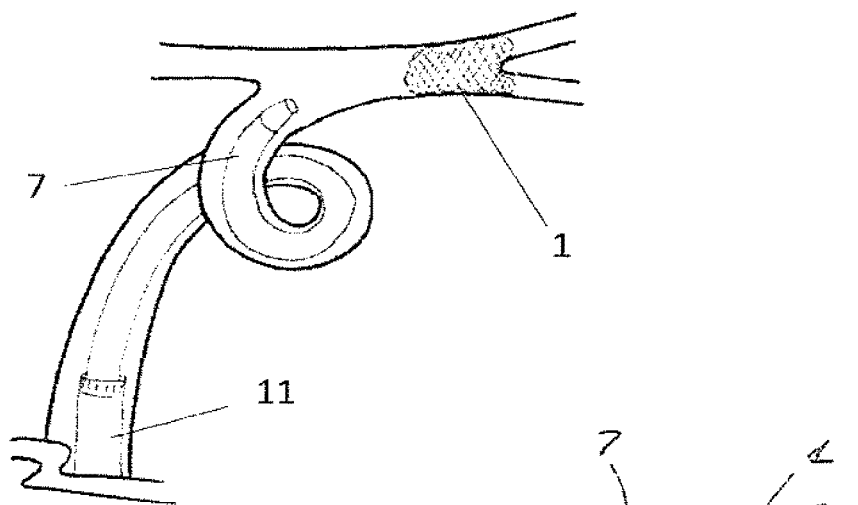
Figure 2B:
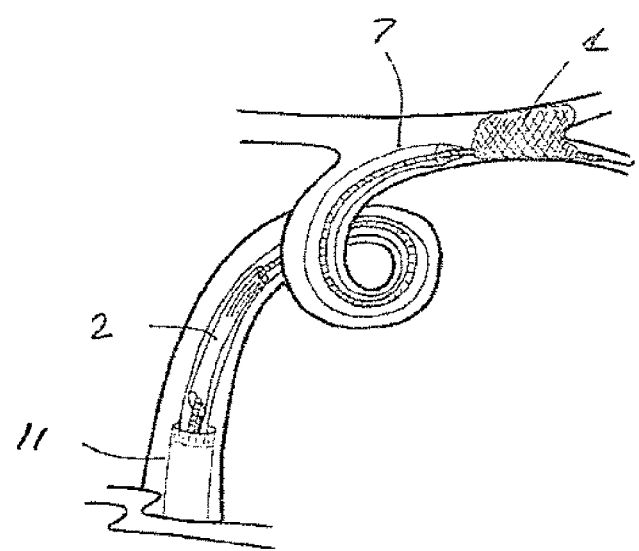
Figure 2C:
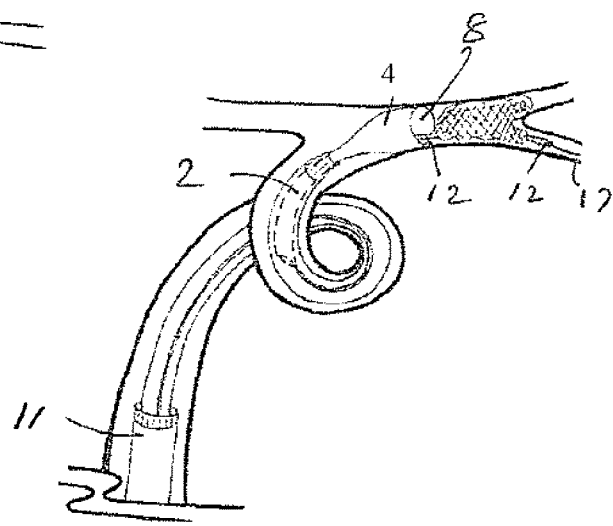

FIG. 1 illustrates a clot receptor device 2 of this invention being used in the retrieval of a clot 1 from the blood vessel of a patient. The clot receptor device 2 comprises an elongate proximal shaft 13 and a tubular expansile distal section 4. The proximal end 5 of the expansile distal section 4 is configured to seal against the inner lumen of a distal section 6 of a catheter 7 through which it is advanced, while the distal end 8 of the expansile distal section is configured to seal against the wall of the blood vessel. The proximal seal against the lumen of the intermediate catheter 7 enables an aspiration force (such as a vacuum or a negative pressure differential, as may be induced by retracting a syringe plunger or through a vacuum pump) to be transmitted through the intermediate catheter 7 to the clot receptor device 2 and thus to the clot. The low profile proximal shaft 13 of the clot receptor device 2 minimizes the space occupied within the intermediate catheter 7, maximising the effectiveness of the transmission of this vacuum/aspiration force to and trough the clot receptor 2. The seal at the proximal end of the clot receptor 2 may be provided by the expansile body of the clot receptor 2 opposing the lumen of the intermediate catheter 7. Other embodiments of this seal include a soft cuff of a foam or fibre construction, or polymer leafs or leaflets, or a balloon cuff, or a stent-like construction with a membrane cover, or combinations of these or other designs The distal end 8 of the expansile distal section 4 is configured to open to a larger diameter than the proximal end, typically at least 50% larger, and in some embodiments up to 500% larger or more, depending on the relative size of the target blood vessel and the lumen of the catheter 7 through which the device is advanced. The large open mouth of the distal end 8 of the clot receptor 2 provides an easy path for retraction of clot into its interior space, and once within this space the clot can be safely retrieved from the patient. In one embodiment the inner lumen of the clot receptor device 2 has a profiled surface (like a sharkskin, or backward facing teeth) which allows clot to slide easily into the device, but resist the clot from escaping back out of the device.

FIGS. 2a to 2f illustrate a typical method of use of such a device and system. The method may include at least some of the following steps: Accessing an arterial blood vessel of a patient using conventional means such as an introducer 10 and guide catheter or sheath 11, advancing a microcatheter 12 up to and across a target occlusive clot with the aid of a guidewire 17, removing the guidewire 17 and advancing a mechanical thrombectomy device 15 such as a stent-retriever through the microcatheter 12 to the target clot 1, retracting the microcatheter 12 at least a few cm to deploy a mechanical thrombectomy device 15 within the clot 1, advancing an intermediate catheter 7 containing the clot receptor device 2 up to a position just proximal of the clot 1 (or within the clot, or considerably proximal of the clot if vessel disease or tortuosity makes access difficult), advancing the clot receptor device 2 up the distal end of the intermediate catheter 7 (or up to and out of the catheter and into or over the clot), retracting the intermediate catheter 7 a short distance to deploy the clot receptor device 2, aspirating through the intermediate catheter 7 using a syringe or pump to suck blood and the target clot into the clot receptor device 2, withdrawing the mechanical thrombectomy device 15 into the clot receptor 2 while continuing to aspirate, withdrawing the clot receptor device 2 and its contents at least partially into the lumen of the intermediate catheter 7, withdrawing the intermediate catheter 7, clot receptor device 2, clot and mechanical thrombectomy device 15 through the guide or sheath 11 and out of the patient.

Many variants of this method are possible.

For example it may be desirable to withdraw the clot 1 and mechanical thrombectomy device 15 through the clot receptor 2, intermediate catheter 7 and guide 11 and out of the patient while leaving the intermediate catheter 7 and clot receptor 2 in place. This allows the physician to retain a protective seal in the vessel to prevent the escape of any clot particles that may be dislodged, and also preserves a means of quick and easy access back to the target site with a microcatheter and thrombectomy device in case additional passes are needed to completely clear the vessel.

Another method variant involves removing the clot receptor device 2 and thrombectomy device 15 together through the intermediate catheter 7, leaving the intermediate catheter 7 in place for easy re-access to the target site.

Yet another method variant involves using the clot receptor device 2 as the primary clot retrieval tool, without the aid of a mechanical thrombectomy device such as a stent-retriever. The clot receptor 2 is configured to expand and seal against the vessel wall adjacent the proximal end of the clot, thus aspirating through the intermediate catheter 7 and clot receptor 2 provides a highly effective suction force to draw the clot into the clot receptor 2. If the clot passes through the clot receptor 2 and into the intermediate catheter 7 it may be aspirated through the intermediate catheter 7 and right out of the patient. If the clot is too large or too firm to pass through the clot receptor 2 then the clot receptor 2 may be withdrawn into the intermediate catheter 7. Because the clot receptor 2 has a smooth and funnel shaped exterior it can be easily retracted into the intermediate catheter 7 even when containing a bulky and/or firm clot.

The distal end 8 of the clot receptor device 2 is intended to open up upon exiting the catheter through which it is delivered to provide a large open mouth approximately equal in size to the inner diameter of the vessel in which it is located and provide a seal against this vessel or significant flow restriction such that when a suction force is applied through the clot receptor 2 this force causes blood and clot distal of the receptor 2 to flow into the receptor 2 rather than blood proximal of the receptor 2. This flow occurs because the pressure inside the clot receptor 2 is lower than that outside (distal and proximal) of the clot receptor 2. If the seal were not present two flow paths into the clot receptor 2 would exist and the less restricted proximal flow path would dominate, reducing the effectiveness of the clot retraction.

In order to adequately seal against the vessel wall the clot receptor 2 should have either a) a high radial force or hoop strength so that the pressure gradient created by the application of suction/aspiration does not collapse the clot receptor or create a flow path past it or b) a seal construction such that the presence of a pressure gradient across the clot receptor 2 serves to tighten the seal rather than reduce it. The geometry and construction of the clot receptor sealing end should be such that it can conform well to the vessel wall, which may be not be effectively circular (such as when close to bifurcations for example, or when inclined at an angle to the vessel wall).

Thus one embodiment of the distal portion of a clot receptor may comprise a self-expanding frame with a relatively non-porous cover, such that the cover prevents any significant passage of blood through the wall of the clot receptor, and the self expanding frame has sufficient radial or hoop strength to resist the pressure gradient created by the application of suction/aspiration. The cover may be a polymeric membrane, or may be a woven or braided or knitted structure. In one embodiment the membrane is a polymer membrane, preferably with a high elastic strain limit and a low modulus to permit its expansion by a low radial force frame structure. A preferred membrane is a polyurethane membrane, which might be extruded or blow moulded or ideally dip coated directly onto the frame. The membrane may be coated with a low friction coating such as a hydrophobic silicone or a hydrophilic material. In one embodiment the membrane is a hydrophilic material itself, comprising a hydrogel with sufficient thickness and modulus to retain its structure under the force of aspiration. Other suitable materials for this cover include PTFE, ETFE and PFA. Materials such as PET, UHMWPE, PET and PEN would be particularly suitable for use in the making of a cover that is woven, braided, knitted or otherwise formed from fibres Another embodiment of the distal portion of a clot receptor may comprise a combination of a self-expanding frame with a relatively non-porous membrane cover, and a plurality of flexible leaflets or vanes disposed around its outer circumference in a manner similar to that of a leaflet valve. In yet other embodiments the additional seal provided by these flexible leaflets is instead provided by an outer cuff, and this outer cuff may comprise a compressible material such as a foam or a hydrogel or a fibre bundle or a shaped polymer.

In yet another embodiment the expansion of the distal end of the clot receptor may be actuatable by the user, by retraction of a pull wire within the device shaft for example, or by inflation of a balloon cuff.

Some of the various embodiments of the distal end of the clot receptor are illustrated in FIGS. 3 to 9.

Figure 3:
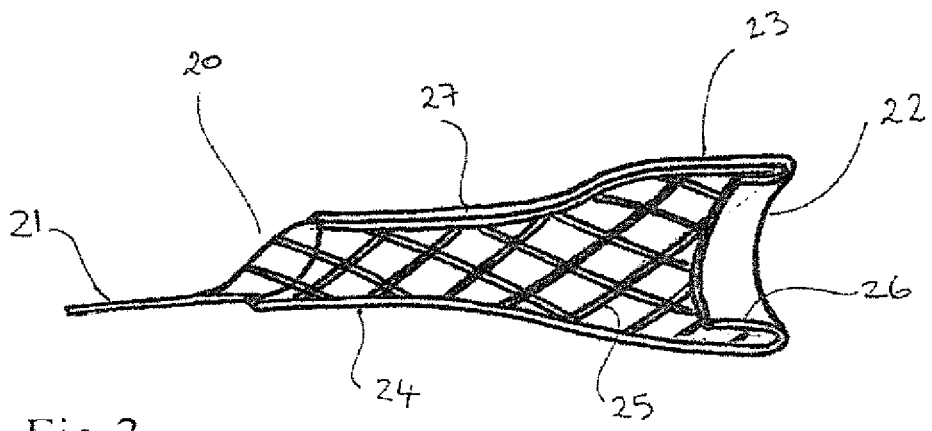

FIG. 3 depicts one embodiment of the distal end of the clot receptor comprising a stent-like self-expanding frame 25 with an outer membrane covering 27. A proximal shaft 21 is connected to the frame and membrane at a proximal entry port 20. The proximal end 24 of the expansile section is configured to gently appose the wall of a catheter through which it is delivered, while the distal end 23 is configured to expand and appose the vessel wall, creating a large opening 22 into the internal reception space. The frame structure 25 is in one embodiment a Nitinol structure laser cut from a tube or sheet, and in another embodiment is a wire structure, wound or braided from Nitinol or stainless steel or other such biocompatible metallic material as are commonly used in the construction of stents or snares. The membrane 27 may comprise a lip 26 which is folded over and wrapped inside the frame 25.

Figure 4:
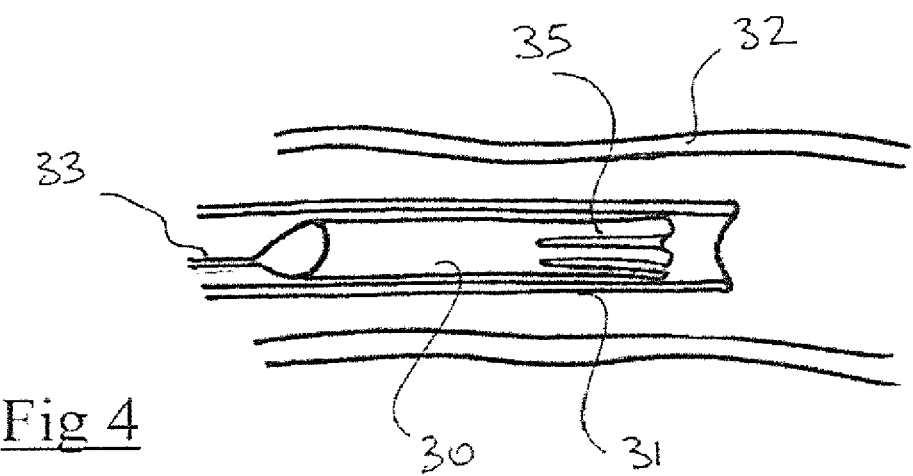
Figure 5:
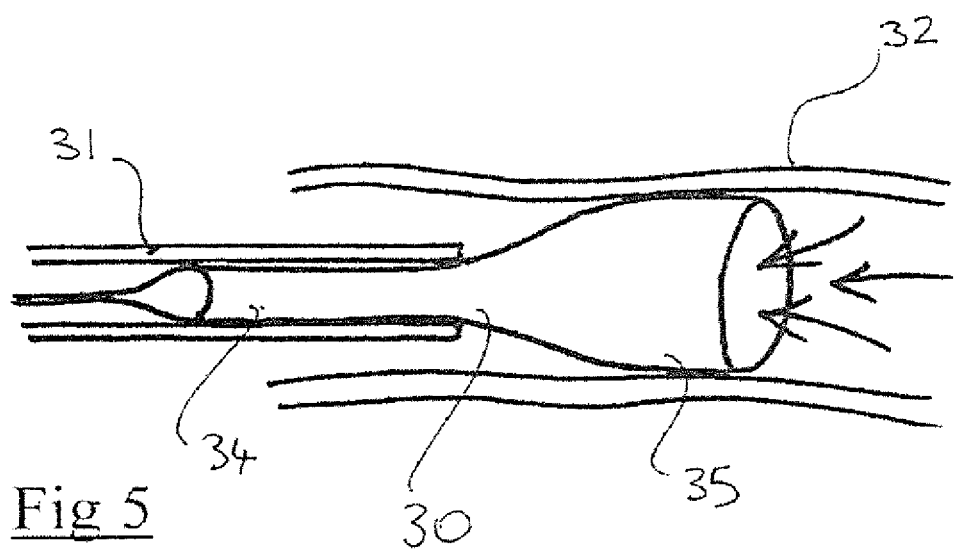

FIGS. 4 and 5 depict a typical embodiment of the distal end of the clot receptor. FIG. 4 shows a clot receptor 30 housed in an outer intermediate catheter 31, positioned in a vessel 32. The distal end 35 of the clot receptor is folded to wrap it into a suitable profile to fit into the lumen of the intermediate catheter 31. FIG. 5 shows the deployed clot receptor upon retraction of the intermediate catheter 31, such that distal end 35 has expanded and is contacting the vessel wall 32, and proximal end 34 is sealing against the inner lumen of the intermediate catheter 31. In another embodiment the distal end 35 expands to a smaller diameter than that of the vessel, but a larger diameter than that of the intermediate catheter.

The intermediate catheter inner lumen may be as small as 0.75 mm or as large as 2.0 mm, but is preferably between 1.0 mm and 1.7 mm. The clot receptor distal end may be configured to expand to a diameter equal to or slightly larger than the target vessel in order to provide a seal, or to a diameter slightly smaller than the target vessel in cases where a low profile, deliverable device is a higher priority than a perfect seal. In one embodiment configured for use in middle cerebral arteries of the brain, the clot receptor distal end is configured to expand to a diameter of between 2 mm and 4 mm. In another embodiment such as might be used in the internal carotid artery, the clot receptor distal end is configured to expand to a diameter of between 4 mm and 7 mm.

FIGS. 6a and 6b illustrate the collapsed (for delivery) and expanded forms of the distal end of a clot receptor 40 of this invention. In this case the mechanism of collapse for delivery through an intermediate catheter is a creasing and folding mechanism, similar to that used to wrap angioplasty balloons. The material of the distal expansile end 42 is configured into pleats or folds 41 to wrap it efficiently into delivery form.

FIGS. 7a and 7b illustrate the collapsed (for delivery) and expanded forms of the distal end of a clot receptor 50 of this invention. In this case the mechanism of collapse for delivery through an intermediate catheter is a rolling mechanism, with an unrolling mechanism taking place for expansion. The distal expansile end 52 exists in its minimum strain state when fully expanded as shown in FIG. 7b. It is configured with a seam 51 running from its distal most end to a point distal of its proximal end. The seam allows the self-expanding clot receptor to be rolled up like a cigarette paper to assume a lower profile shape for delivery.

FIGS. 8a and 8b illustrate the collapsed (for delivery) and expanded forms of a frame 60 of the distal end of a clot receptor of this invention. This frame may be formed from Nitinol or another material with a sufficient elastic strain limit such that this limit is not exceeded when the device is collapsed for delivery through an intermediate catheter. In one embodiment the frame is laser cut from a Nitinol tube or sheet, and comprises struts 61 connected at crowns 62. The distal end of the frame comprises terminal crowns 63, which may be formed with atraumatic ends of a higher radius of curvature than that used for the more proximal crowns. The frame may be covered with a polymeric membrane as described earlier.

FIG. 9 illustrates the expanded form of a frame 70 of the distal end of a clot receptor of this invention, which is similar to frame 60 of FIG. 8 but is formed from wires 73 rather than cut from a tube or sheet. One advantage of such a structure is that non superelastic materials (such as SS, MP35N or other materials commonly used in the manufacture of balloon expandable stents) can be used in its construction. This is because a much lower strain is induced in the frame in moving from its expanded to collapsed state, because the wires are free to move and slide relative to one another, even at crossover points 72. The wires form crowns 71 of a large and gentle radius at the distal end of the frame, rendering the tip of the device atraumatic to a blood vessel.

Figure 10:
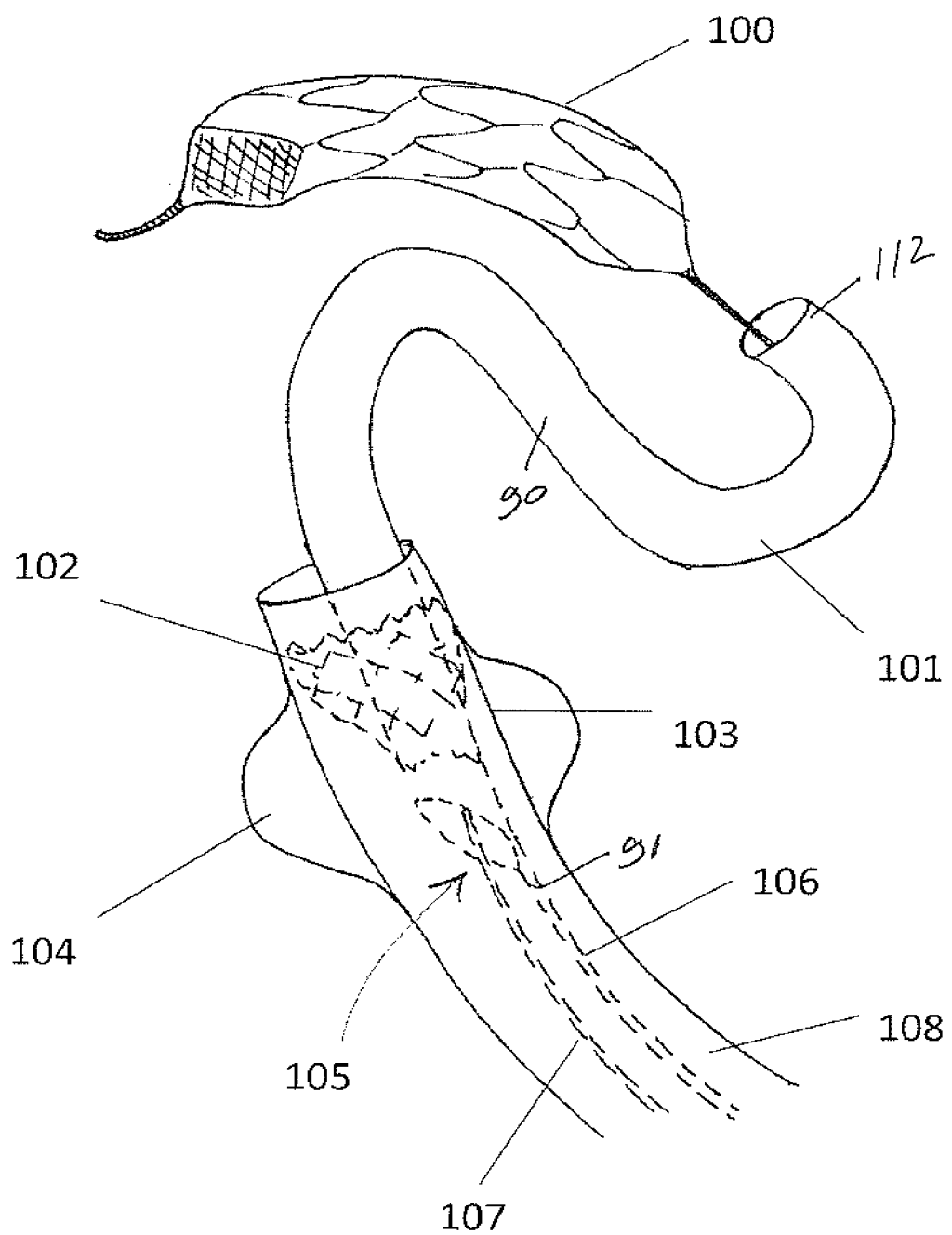
FIGS. 10 and 11a to 11d illustrate a rapid exchange aspiration catheter according to the invention.
Figure 11A:
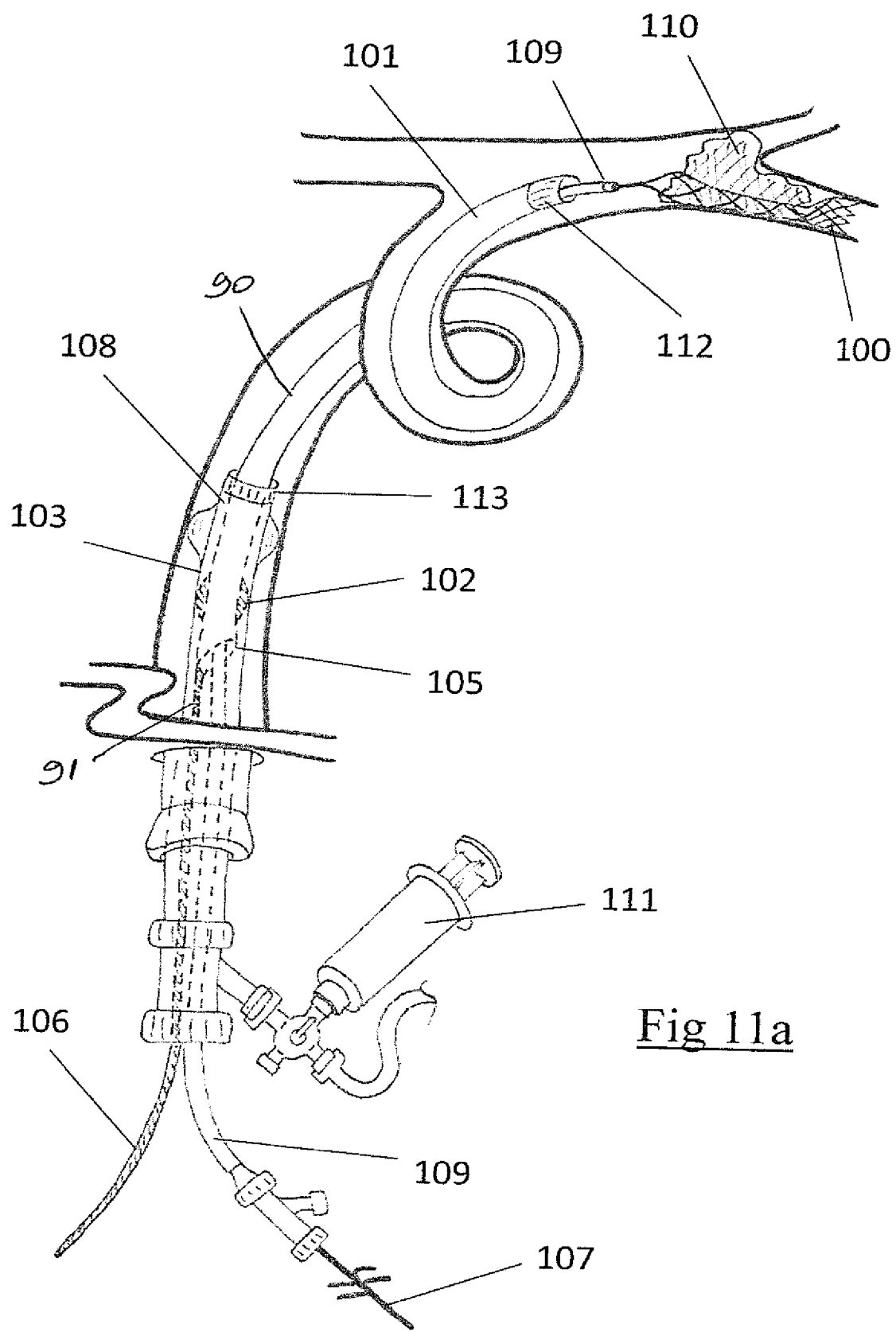
Figure 11B:
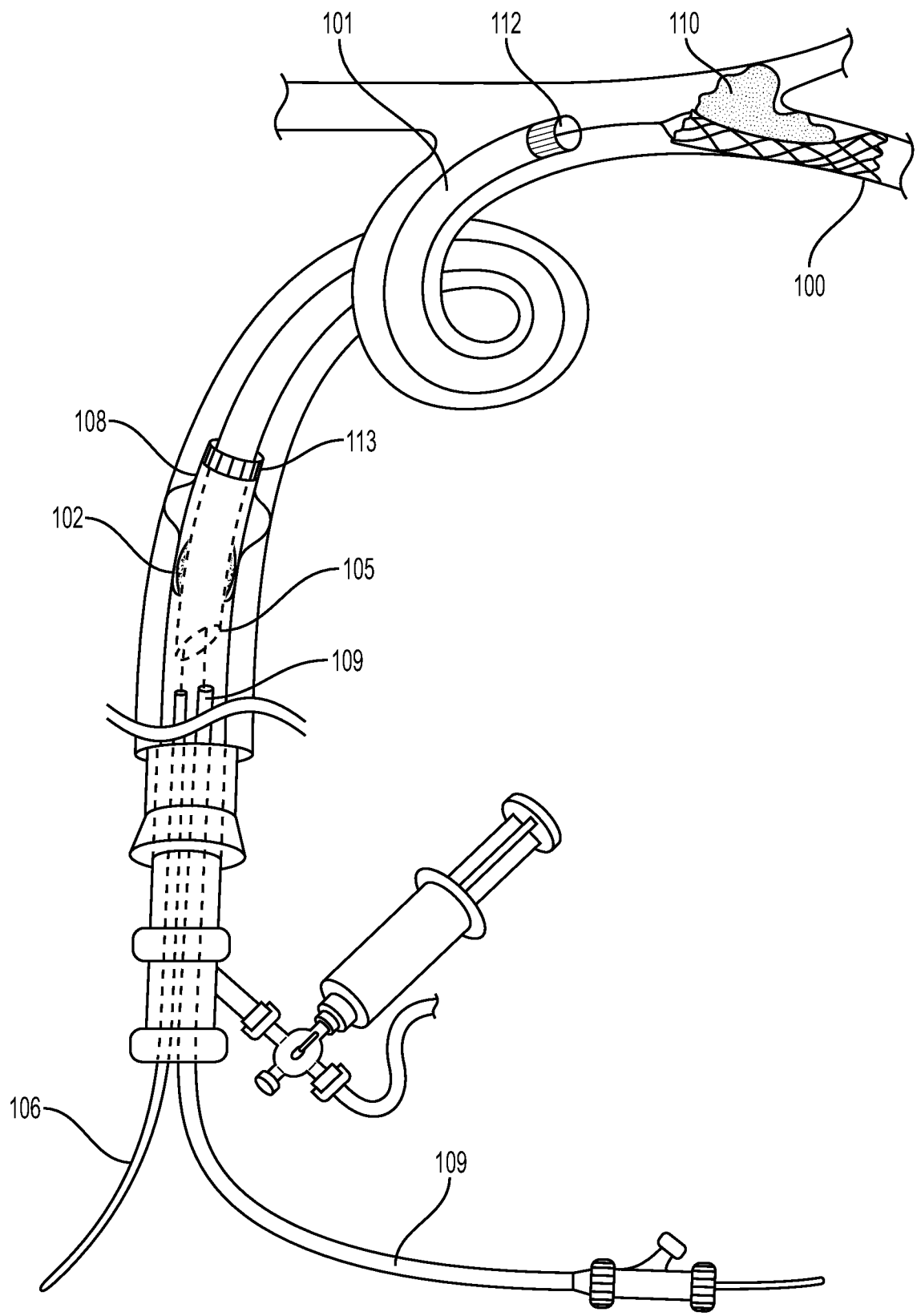
Figure 11C:
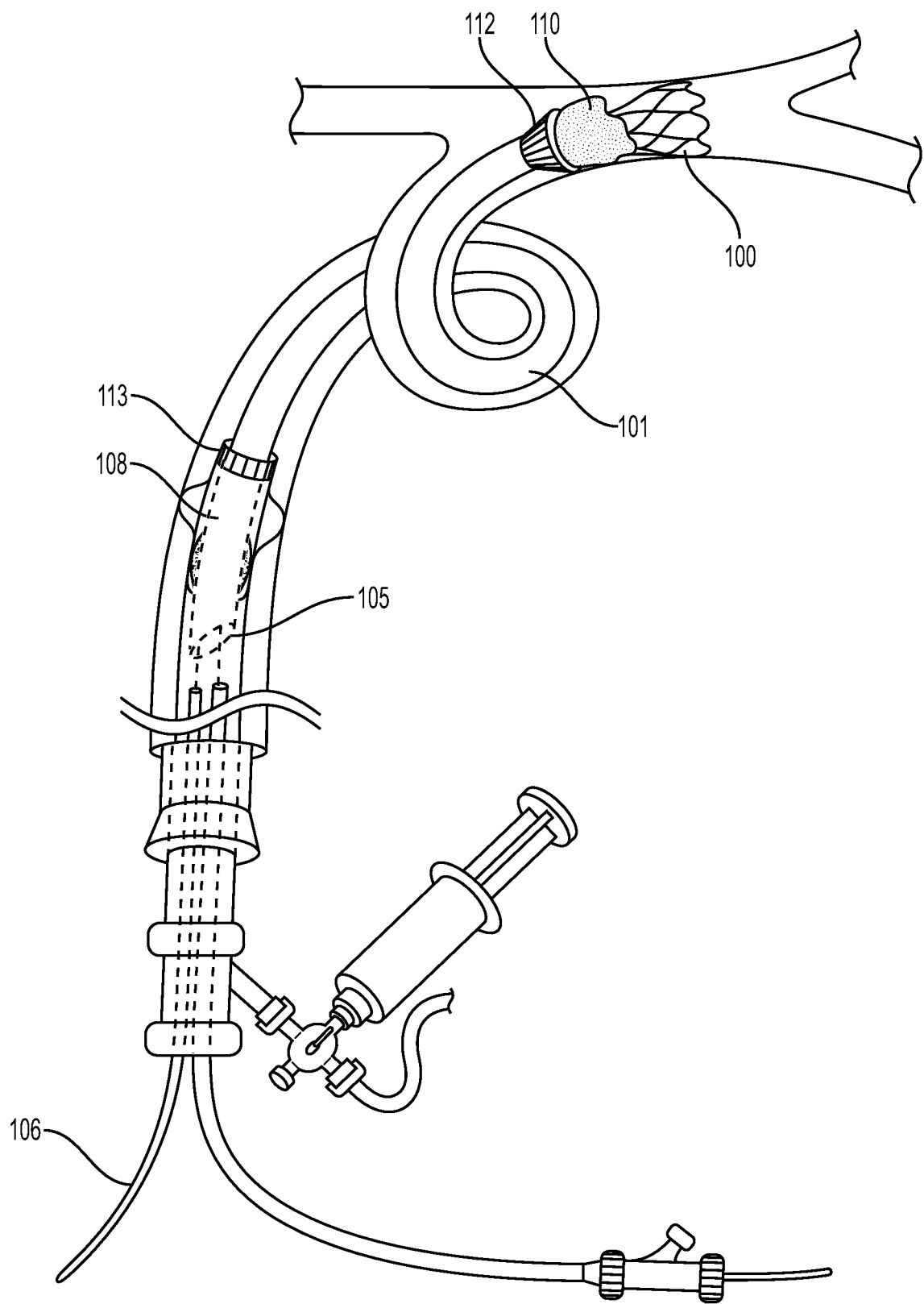
Figure 11D:
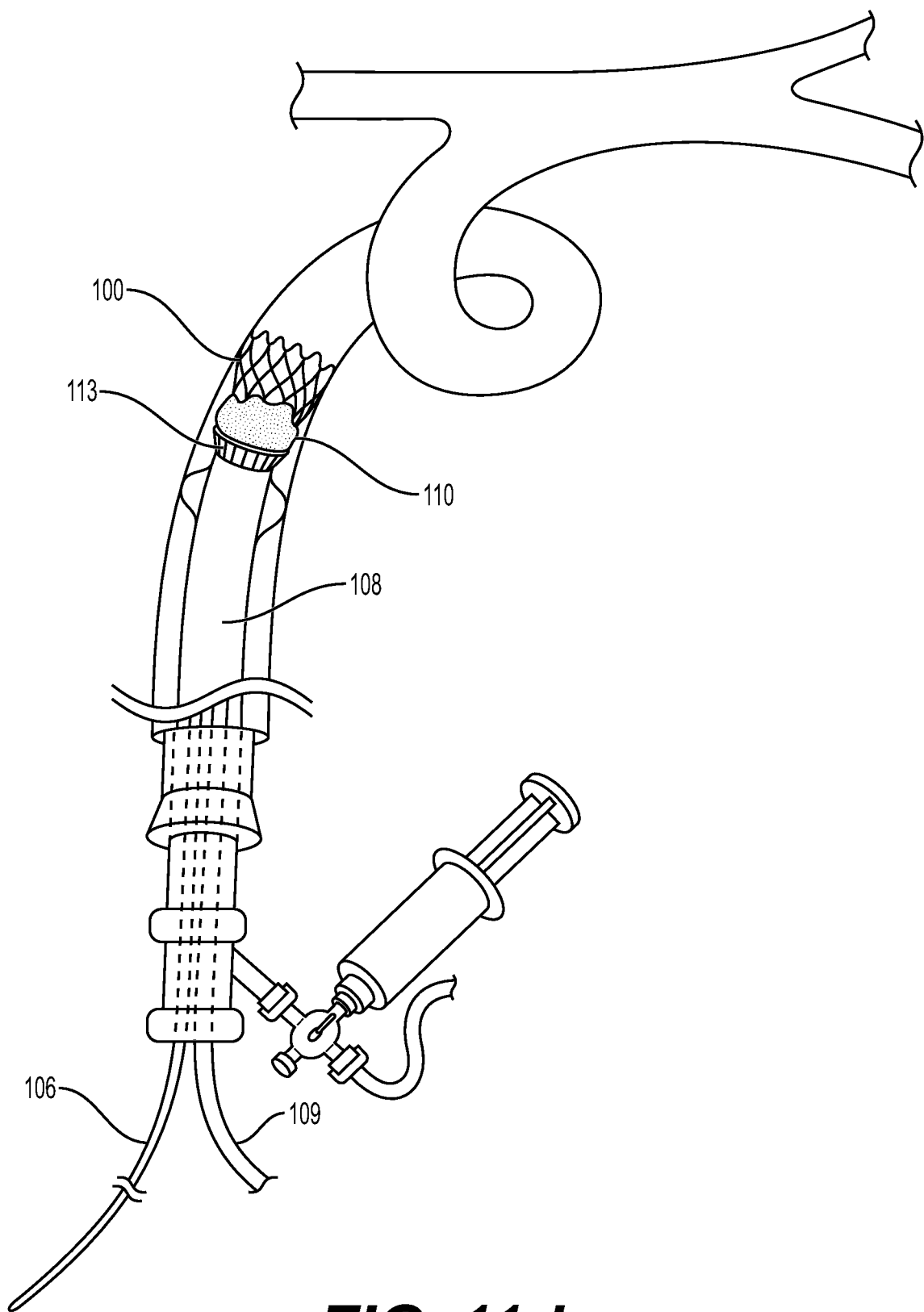

Referring to FIGS. 10 and 11 there is illustrated an aspiration catheter 101 according to the invention. In FIG. 11a the aspiration catheter 101 is illustrated as part of a clot retrieval system for retrieval of a clot 110. The clot retrieval system further comprises a clot engaging device 100, a microcatheter 109 through which the clot engaging device is delivered and a guide catheter 108 through which the aspiration catheter 100 and microcatheter 109 are delivered. The aspiration catheter 101 comprises a distal segment 90 and a proximal segment 91. The distal segment 90 comprises a distal end provided with a distal tip 112 and a proximal end provided by a transfer port 105. A lumen of the distal segment 90 extends proximal of the distal end 112 and terminates at the transfer port 105. The proximal segment 91 extends from the distal segment 90 and in this case is provided by a proximal shaft 106. A flow restrictor 102 is located on the outer surface of the aspiration catheter 101 distal of the transfer port 105. The aspiration catheter 101 provides a proximal seal 102 against a guide catheter inner lumen 103 so that aspiration may be applied through the guide catheter 108 and thus take advantage of a large proximal lumen.

FIG. 10 shows a simplified view of a distal region of the system, illustrating more clearly how the aspiration catheter flow restrictor 102 interacts with the inner lumen of the guide catheter 108. The guide catheter 108 may also have a flow restrictor component such as the inflatable balloon portion 104 shown in this illustration.

The aspiration catheter 101 is a rapid exchange (RX) catheter in which the exit port 105 defines a transfer port for aspiration and provides a deliverability advantage of minimal frictional engagement with the guide catheter 108 proximal of the exit port 105.

In some cases a microcatheter 109 may be provided through which a clot capture device 100 is delivered. Retracting the microcatheter 109 just proximal of the exit port 105 (rather than completely removing it) creates large aspiration advantage.

In one case the microcatheter 109 and the Rx aspiration catheter 101 are introduced together into the guide catheter 108.

The guide wire and microcatheter 109 are then advanced across the clot 110. The guidewire can be removed and a clot retrieval device such as a stent retriever device 100 is introduced.

Using the microcatheter 109 for support, the Rx aspiration catheter 101 can be forwarded to a position proximal to the clot 110 by pushing the proximal shaft 106 or handle into the guide catheter 108. The stentriever device 100 can be deployed by retracting the micro catheter 109.

The Rx aspiration catheter 101 can then be forwarded to contact the clot 110 or be positioned just proximal to or at the proximal face of the clot 110. The microcatheter 109 can then be retracted sufficiently to be proximal of the Rx port 105 of the Rx aspiration catheter 101. This facilitates an increased lumen for aspiration without the necessity of removing the microcatheter 109 fully from the intermediate/aspiration catheter.

Aspiration can be applied to the lumen of the guide catheter 108 with a manual syringe 111 or vacuum pump. This aspiration is directed to and effective at the distal tip 12 of the Rx aspiration catheter 101 due to the presence of the flow restrictor or seal 102 between the outer surface of the Rx aspiration catheter 101 and the inner guide catheter 108. This seals the lumen between the outside of the Rx aspiration catheter 101 and the inner lumen 103 of the guide catheter 108 and prevents backflow of blood into the tip of the guide catheter 108 which would reduce the effectiveness of the aspiration. The seal 102 may not need to stop flow in the lumen completely but needs to restrict flow sufficiently so as not to have a significant effect on aspiration performance. This seal 102 can be generated in a number of ways such as those described in FIGS. 12 to **13*l*. In some cases the seal 102 is located on the inside surface of the guide catheter 108 and/or on the outside surface of the aspiration catheter 101**.

The Rx aspiration catheter 101 is constructed of a proximal handle (not shown) to facilitate grip and a proximal shaft 106 constructed from a wire or tube formed preferably from Nitinol, stainless steel, PEEK or some other similar material. An additional seal may be provided on a proximal haemostasis valve to assist in sealing against the proximal shaft 106. The material of the shaft 106 has high compressive and tensile strength and may have a low friction coating or jacket to minimise insertion and retraction forces. The low friction coating or jacket could be formed from PTFE, HDPE or a similar material.

The Rx exit port 105 on the aspiration catheter 101 can facilitate forwarding a microcatheter 109 through the port 105 and through the distal section 90 of the Rx catheter 101 prior to insertion into the guide catheter 108. The Rx exit port 105 may be formed in a funnel shape to make it easier to forward a microcatheter 109 into the port even in position in the guide catheter 108. The port 105 may be formed from a moulded component or from the tubing of the distal section 90 of the catheter 101.

The distal section of the Rx aspiration catheter 101 has good push and trackability characteristics to allow it to be forwarded to the target location. Therefore it may be constructed of one or more materials to give a reducing stiffness profile along the length. A braided wire or coil wire construction or combination of both may be used to improve compressive strength and track ability. Linear wire supports running parallel to the tube axis may also be used.

A top layer of low friction material may be applied to the distal section of the catheter 101 or alternatively a hydrophilic coating or silicon oil coating may be applied to the surface. The inner lining of the distal section of the catheter 101 consists of PTFE or similar low friction material to minimise insertion and retraction forces.

Figure 12A:
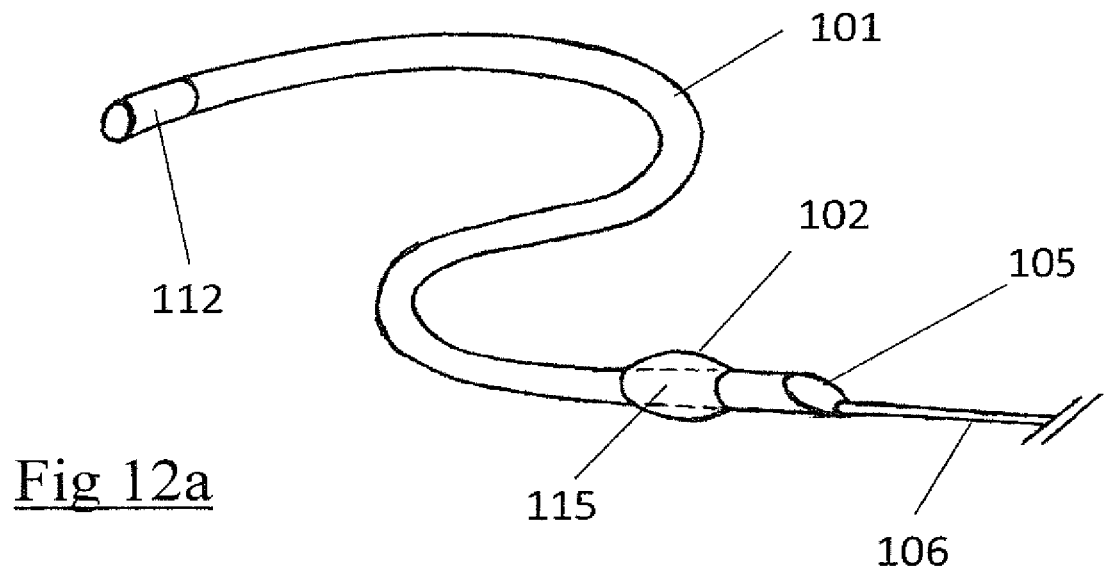
FIGS. 12a, 12b, and 13a to 13L illustrate various proximal and distal seals.

The seal 102 on the outer surface of the Rx aspiration catheter 101 distal section 90 prevents or significantly reduces blood flow travelling from the guide catheter distal tip 113 to the Rx port 105 of the Rx aspiration catheter 101 as shown in FIG. 12*a*. Various embodiments of proximal seals 102 are illustrated in FIGS. 12 to **13*l***.

Figure 12B:
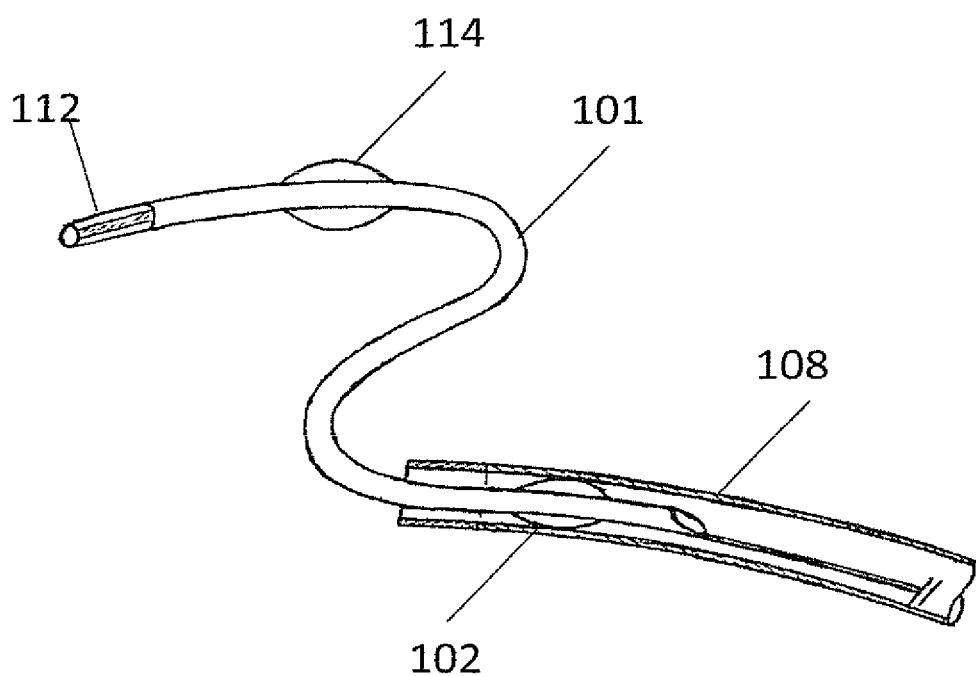

In another embodiment of the device shown in FIG. 12*b* an additional seal 114 is provided on the distal end of the catheter 101 to seal between the Rx catheter and the target vessel. This seal 114 is spaced distally from the proximal flow restrictor 102 and occludes blood flow in the vessel and improves aspiration effectiveness without the need for a balloon guide catheter. The seal 114 can be constructed in a similar manner to those shown in FIGS. 12*a* to **13*l***.

Figure 13A:
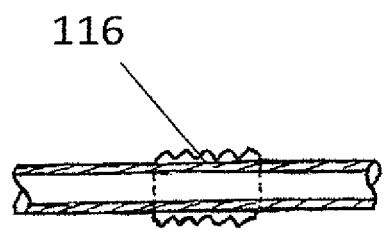
Figure 13B:
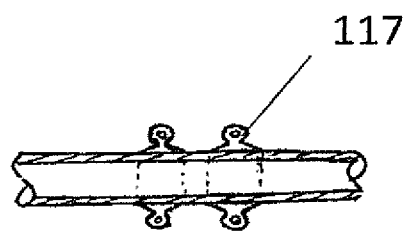
Figure 13C:
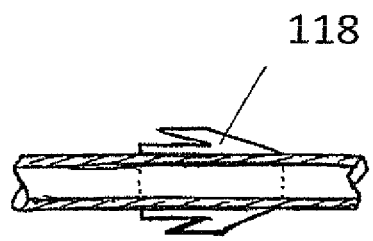

The seal 102 can be formed from an outer sleeve on the catheter which may be smooth or have a grooved or profiled surface 116 as shown in FIG. 13*a*. FIG. 13*j* shows a profiled surface with a spiral groove 125. The seal could also be formed from one or more moulded rings with a sealing lip or "O" ring profile 117 as shown in FIG. 13*b*. It could also be formed from an inflatable balloon 115 which is inflated by injecting saline through a lumen in the shaft and catheter as shown in FIGS. 12*a*, 12*b* and 13*g*.

Figure 13D:
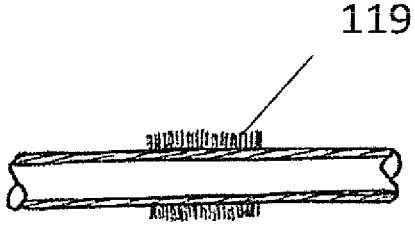
Figure 13E:
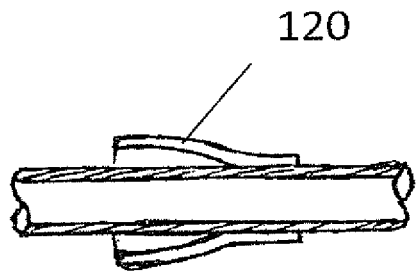
Figure 13F:
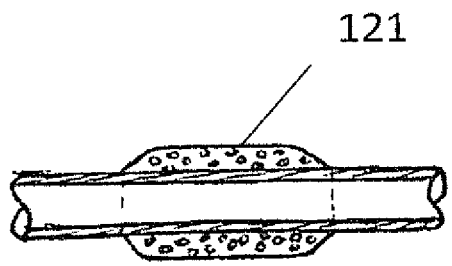
Figure 13G:
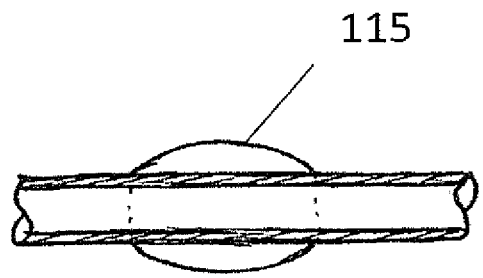
Figure 13H:
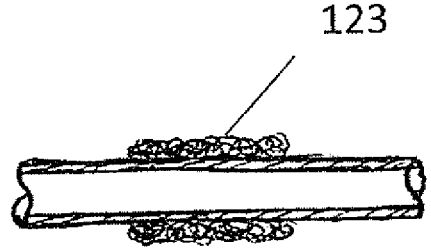
Figure 13I:
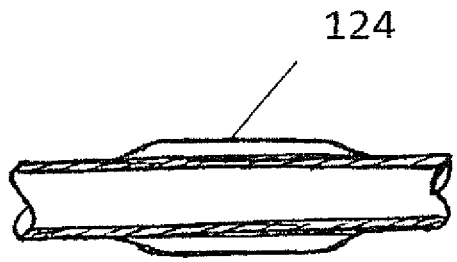
Figure 13J:
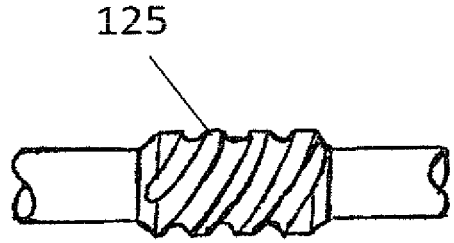

In another embodiment illustrated in FIG. 13*d* the seal 102 can be constructed of fibres in a brush/bristle configuration 119 or from a fibre mesh 123 formed of PET fibres or similar material as shown in FIG. 13*h*. Similarly the seal could be formed of a sponge material 121 which is compressed when inserted into the lumen of the guide catheter 108 as shown in FIG. 13E In a further embodiment the seal 102 could be provided by a body 124 formed from a hydrophilic 124 or similar material which swells and increases in diameter when in contact with saline or blood. The seal 102 may also be formed by having a close tolerance clearance fit between the outer diameter of the distal end of the Rx aspiration catheter 101 and the inner diameter of the guide catheter 103. In another embodiment, the seal 102 is formed from a lip 118 or membrane 120 which restricts flow particularly in one direction as shown in FIGS. 13*c* and 13*e*.

Figures 13K, 13L:
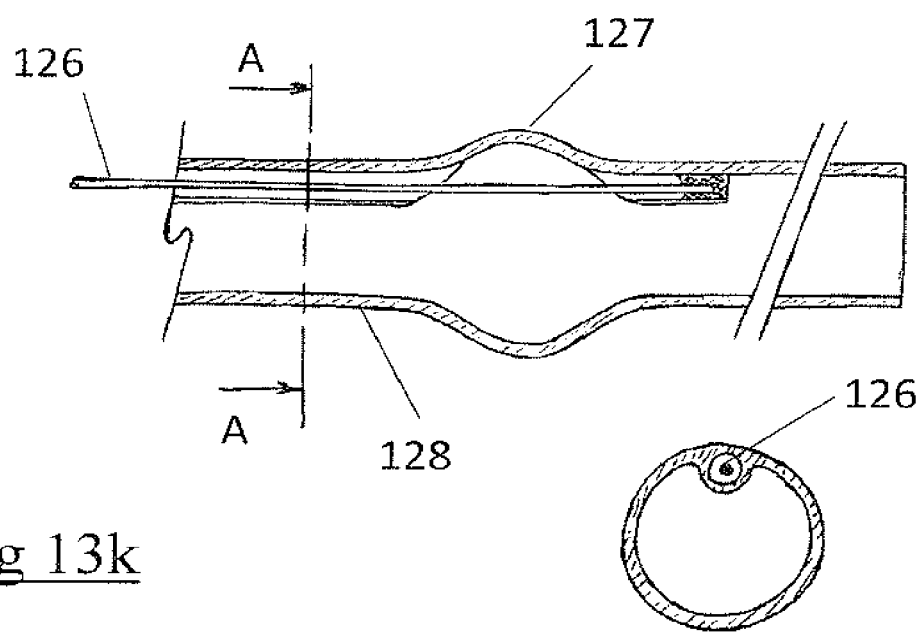

In another embodiment of the seal 102 shown in FIGS. 13k and 13l, the occlusion between the Rx aspiration catheter 101 and the guide catheter 108 is achieved through longitudinal compression of the aspiration catheter 101. This can be achieved by having an expansile section 127 which increases in diameter when the catheter is under compression. The compression can be a result of retrieving clot 110 and the stentriever device 100 into the tip 112 or may be manually actuated through a pull wire 126. This pull wire 126 may run through a separate lumen from the proximal end of the device as shown in the cross sectional view A-A in FIG. 13l.

The clot 110 and stentriever type device 100 can be fully or partially retrieved into the Rx aspiration catheter 101 as controlled by the physician and depending on the resistance felt by the user or clot obstruction of the lumen as indicated by an increase in vacuum/loss of suction. The expansile tip 112 of the Rx aspiration catheter 101 facilitates aspiration and retrieval of the clot 110 and stentriever device 100 by expanding under load to reduce the retraction force and lessen the risk of scraping clot off the surface of the stentriever device 100. The expansile tip 112 can also partially or fully occlude the vessel providing flow arrest improving aspiration effectiveness.

The expansile tip 112 can be formed in a number of ways and various embodiments are shown in FIGS. 14 to 37.

Figure 14:
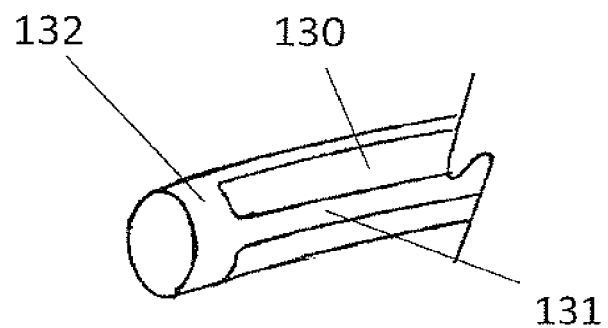
Figure 15:
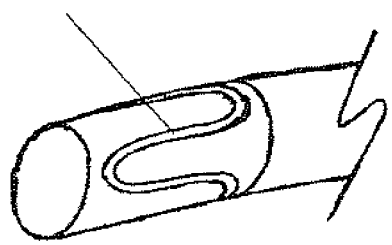
Figure 16:
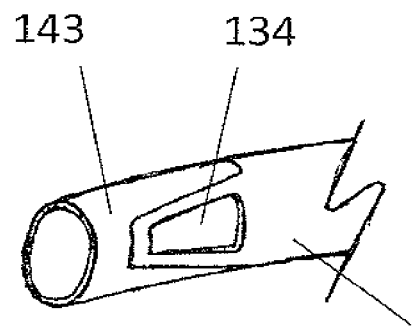
Figure 17:
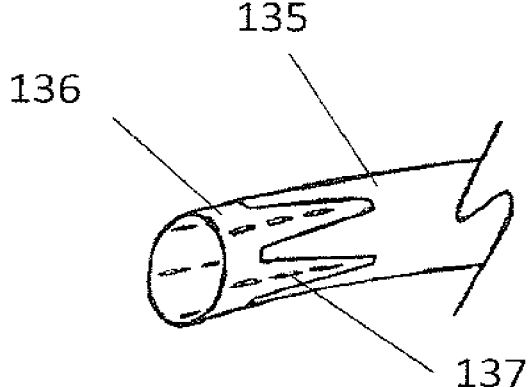
Figure 18:
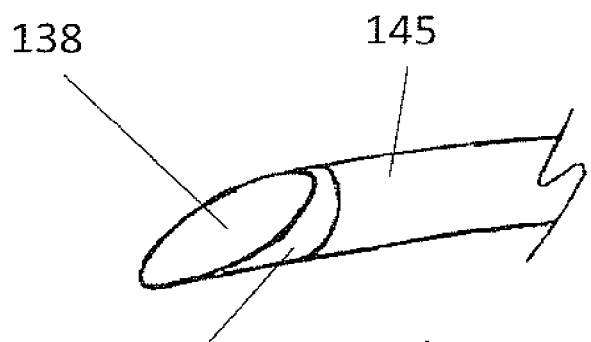
Figure 19:
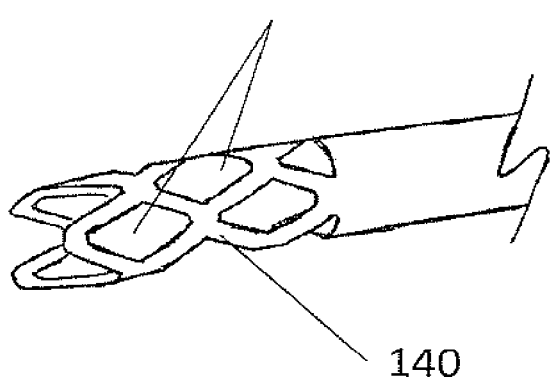
Figure 20:
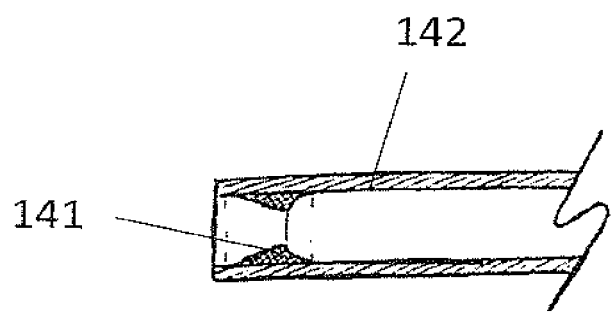
Figure 21:
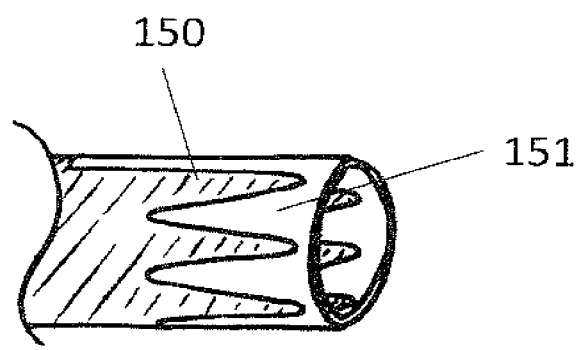
Figure 24:
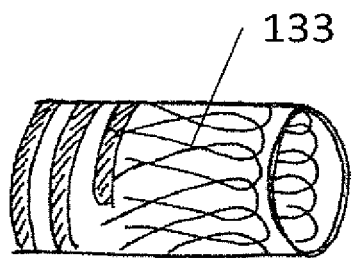
Figure 25:
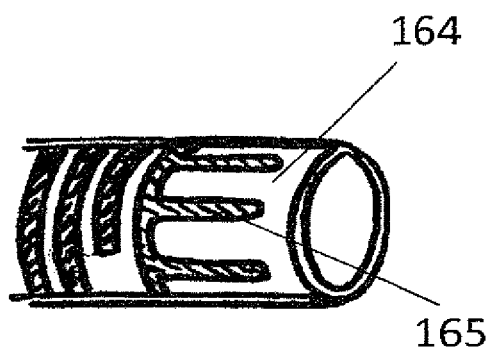

In one embodiment the expansile tip 112 can be formed from a co-extrusion of materials with different properties such as a soft expansile polymer 131 co-extruded with a higher modulus polymer 130 to provide longitudinal support. A fully expansile ring 132 could then be connected to this tip as shown in FIG. 14. The tip 112 may also include one or multiple metallic wire supports 133 as shown in FIGS. 15 and 24. In another embodiment shown in FIG. 18 the tip has a skived profile to increase contact area with the clot during retrieval or aspiration. The tip may be formed with holes 134 or perforations 137 to allow it to split and change shape when a device 100 and clot 110 is retracted into the tip as shown in FIGS. 16 and 17. These features can be combined with tip constructions containing materials of different durometers such as shown in FIGS. 16, 17, 18, 21 and 25. In these embodiments the tip materials 143, 136, 146, 151, 164 have a lower durometer and are more expansile than the support materials 135, 144, 145, 150, 165. These support materials may be embedded within the wall of the tubing or may be on the inner or outer surface. They may also be formed in a spline, coil, stripe, 'U' shape or other configuration to provide longitudinal support to the expansile material to prevent it collapsing or buckling under compressive load, such as occurs during retrieval of a clot or stentriever device, or during insertion through a guide or access catheter. FIG. 19 shows another embodiment where multiple holes 139 produce a lattice or framework in the tip. Single or multiple protrusions or "teeth" 141 may also be applied to the inner surface 142 at the distal tip to improve grip on the clot as shown in FIG. 20.

The expansile tip may be pre shaped to form a flared profile (FIG. 22a) or a tapered profile as shown in FIG. 22b. Alternatively the tip shape may be a combination of these profiles such as bulbous or 'pear' shaped as shown in FIGS. 23a to 23d. In the configuration shown in FIG. 23a the tip 160 has an increased diameter larger than the proximal catheter diameter 161 which then tapers to a reduced diameter 162 for ease of insertion. In the configuration shown in FIG. 23b the tip 166 has an increased diameter larger than the proximal catheter diameter 161 which then tapers to a reduced diameter 167, however the reduced diameter 167 is still larger than the proximal catheter diameter 161. This tip configuration provides benefits of improved aspiration effectiveness and reduced retrieval force but also low insertion force and trackability benefits due to the distal tip radius or taper 167. The tip radius 167 also prevents the tip snagging on a bifurcation on insertion, such as at the ostium of the ophthalmic artery in the internal carotid artery. FIG. 23c shows how the tip 160 elongates during insertion through a guide or access catheter 108, while FIG. 23d shows the tip 160 expanding to accommodate the retrieval of a clot 110 and stentriever device 100. The profiled tips can also be constructed using multiple materials of varying durometer and expansile characteristics.

Figure 26:
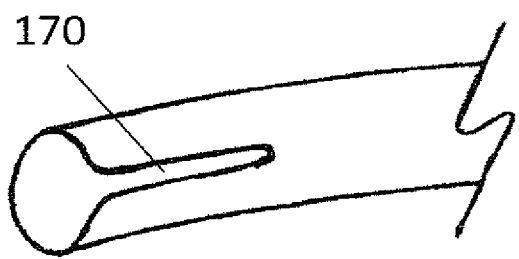
Figure 28:
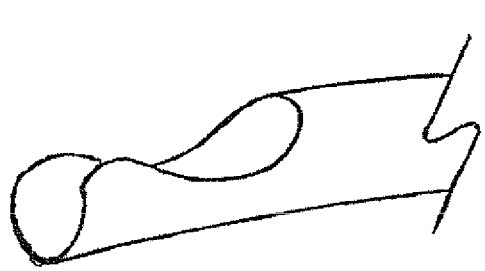
Figure 27:

The expansile tip 112 could also be profiled and contain one or more slot cuts 170 to facilitate expansion as shown in FIGS. 26, 29 and 30. Other embodiments of profiled tips to facilitate expansion and retrieval of the clot 110 and stentriever device 100 are shown in FIGS. 27 and 28.

In another embodiment of the Rx aspiration catheter tip 112 shown in FIG. 31, the distal end of the tip has a collar 171 which tracks closely over the guidewire. This helps direct the catheter over the guidewire to the target location reducing the risk of snagging. The tip configuration shown in FIG. 32 has a flattened section 173 which contains a large number of aspiration pores 174, and aspiration windows 172. This design potentially increases the contact area with the clot improving grip where the catheter is used without a stentriever device. FIG. 33 shows an end view of FIG. 32 with the arrows indicating the direction of blood flow.

Figure 34A:
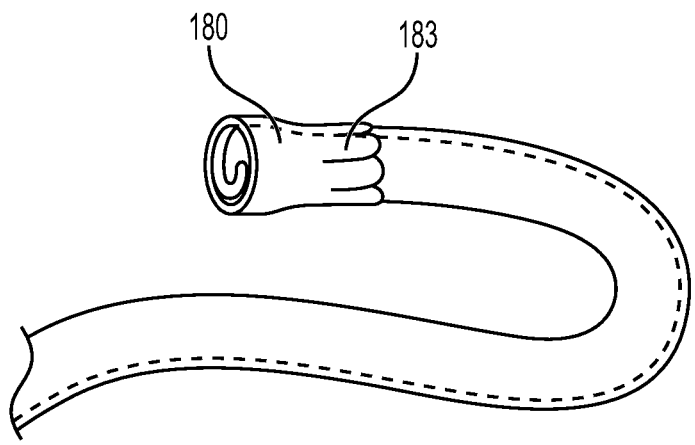
Figure 34B:
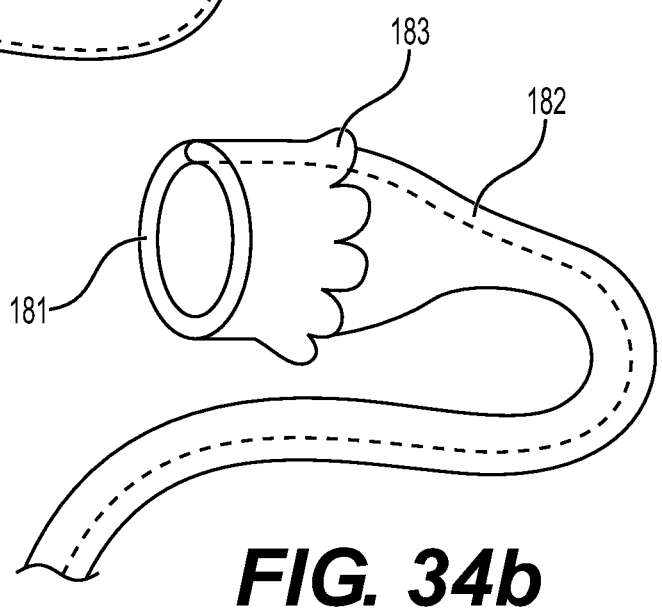
Figure 35:
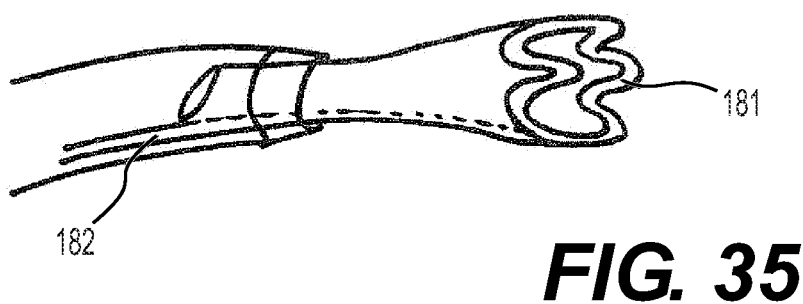

Referring to FIGS. 34 to 35 there is illustrated a catheter with an expandable distal end 180, which is expanded by means of a lifebelt shaped annular balloon 181 at or adjacent its distal end. The balloon is inflated by injecting a fluid through an inflation lumen 182 running from the proximal to distal end of the device. The distal end of the catheter has a ring of petals 183 which act as a seal or occluder to limit the volume of blood flowing from proximal of the tip into the catheter, when aspirating through the catheter. The petals 183 may be formed from a polymeric material. FIG. 34a shows the tip in the collapsed configuration and FIG. 34b shows the tip when the annular balloon 181 is inflated. FIG. 35 shows an additional embodiment where the catheter has an Rx construction with the inflation lumen 182 running through the shaft to the proximal end of the device.

Figure 36A:
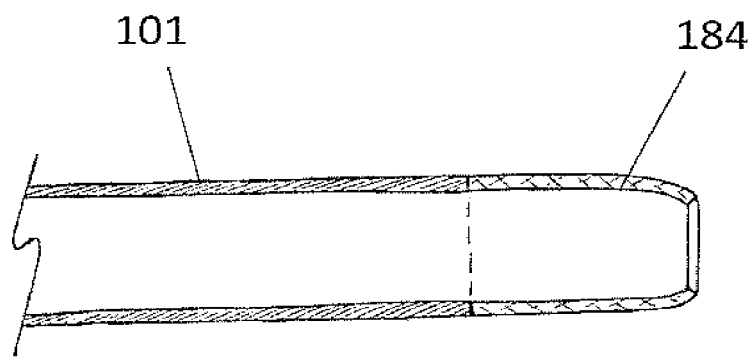
Figure 36B:
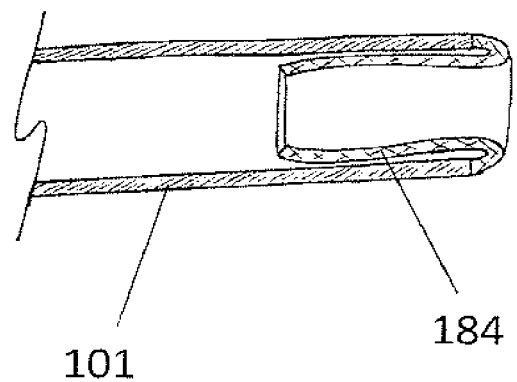

In another embodiment of the catheter tip 112, shown in FIGS. 36a and 36b, the tip 184 is constructed so that it can invert as the stentriever device 100 and clot 110 are retrieved into the catheter. This can reduce the retraction force and constrain the clot so fragments are not released during the retrieval process. FIG. 36b shows the tip after inversion.

Figure 37A:
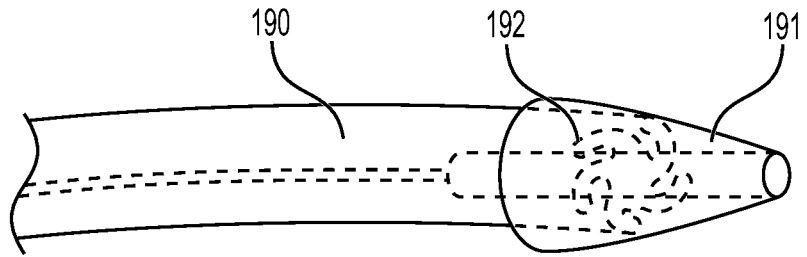
Figure 37B:
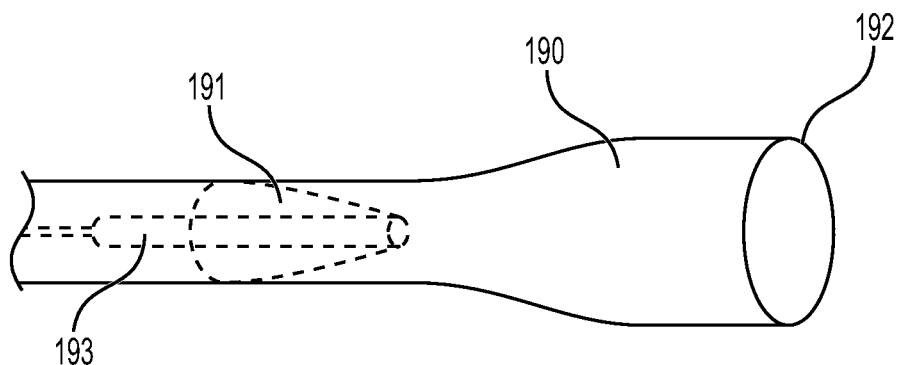

Referring to FIGS. 37a and 37b there is illustrated a clot retrieval catheter with a self-expanding distal tip 190 that is constrained by a tapered cap 191 for ease of deliver and atraumatic access to a target site. The cap component 191 can be retracted to allow the catheter mouth 192 to expand, creating a large opening to accept clot or other material into its lumen. The cap component 191 has a distal end whose outer diameter is ideally lower than that of the catheter shaft immediately proximal of the cap, and an inner lumen sized to enable the device to be advanced over a thrombectomy device shaft and microcatheter. The cap component 191 may also comprise a guide tube 193 to aid the device in moving smoothly over a thrombectomy device shaft or microcatheter.

Figure 38:
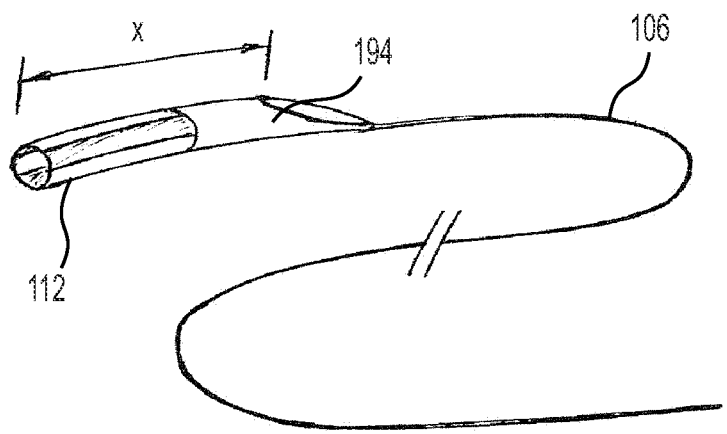
FIG. 38 illustrates an alternative rapid exchange configuration

In another embodiment of the device shown in FIG. 38 the distal section of the catheter 194 is shortened so that distance X is typically between 5 and 50 mm long. This device can be forwarded over the shaft of the stentriever device 100 to the target location to facilitate partial or full retrieval of the stentriever 100 into the expansile tip 112. In this embodiment the distal section 194 is forwarded out of the guide catheter 108 and does not translate aspiration to the distal tip 112, but has improved trackability and access performance to reach the target vessels due to reduced friction and pushability of the wire shaft. The short length distal section 194 and tip 112 are connected to a shaft 106 constructed from a wire or tube formed preferably from Nitinol, stainless steel, PEEK or some other similar material. The shaft material has high compressive and tensile strength and has a low friction coating or jacket to minimise insertion and retraction forces. The expansile tip 112 can be constructed in a similar manner to those shown in FIGS. 14 to 37.

The Rx aspiration catheter 101, microcatheter 109, stentriever device 100 and clot 110 can be retracted as a unit back to the tip of the guide catheter 113 and then fully into the guide catheter 108. The guide or access catheter 108 may also have an expansile tip 113 to facilitate retraction of the devices and clot, with a reduced force and lower risk of dislodging the clot from the devices. This expansile tip 113 on the guide catheter may be constructed in a similar manner to those shown in FIGS. 14 to 37. Likewise the expansile tip 112 construction and seal 102 construction shown in FIGS. 12 to 37 may also be applied to a standard length intermediate or aspiration catheter.

The Rx aspiration catheter 101, microcatheter 109, stentriever device 100 and clot 110 can then be retrieved from the guide catheter 108 and removed fully from the patient.

Referring to FIGS. 39 to 46 there is illustrated a removable microcatheter hub according to the invention. The removable hub enables a physician to advance an intermediate or access catheter over the microcatheter after the microcatheter (and thrombectomy device) are already in position (as bail out for example). It is not possible with a standard microcatheter to forward an intermediate or access catheter over the proximal end as the fixed hub is in the way, therefore the standard microcatheter has to be removed to introduce an intermediate catheter.

Use of a microcatheter with a removable hub that facilitates the use of an extension wire facilitates improved control on the microcatheter position as the intermediate catheter is introduced.

In FIGS. 39 to 46 the following numerals are used:
300 detachable hub
301 microcatheter shaft
302 strain relief element extending from microcatheter hub
303 internal connector (see FIGS. 42/43 for detail)
304 end of microcatheter shaft which has detached
305 extendable shaft for intermediate catheter exchange
306 internal thread on microcatheter hub
307 microcatheter connector
308 O-ring seal
309 external thread on microcatheter connector
310 bond
311 closed end to prevent outbleed
312 bond
313*a* extension wire
313*b* extension wire housing
314 laser cut hypotube which acts as a core reinforcement for microcatheter
315 stiff proximal shaft so that it can be gripped and pulled/twisted during microcatheter removal
316 compressible O-ring which locks the microcatheter into recess incorporated into moulded catheter hub
317 detachable hub
318 extension tube
319 spring clip—e.g. stainless steel or Nitinol
320 injection moulded hub
D1 0.021 inch ID approx.
D2 0.029 inch OD approx.
D3 0.039 inch OD approx.
D4 0.045 inch OD approx.

Figure 39:
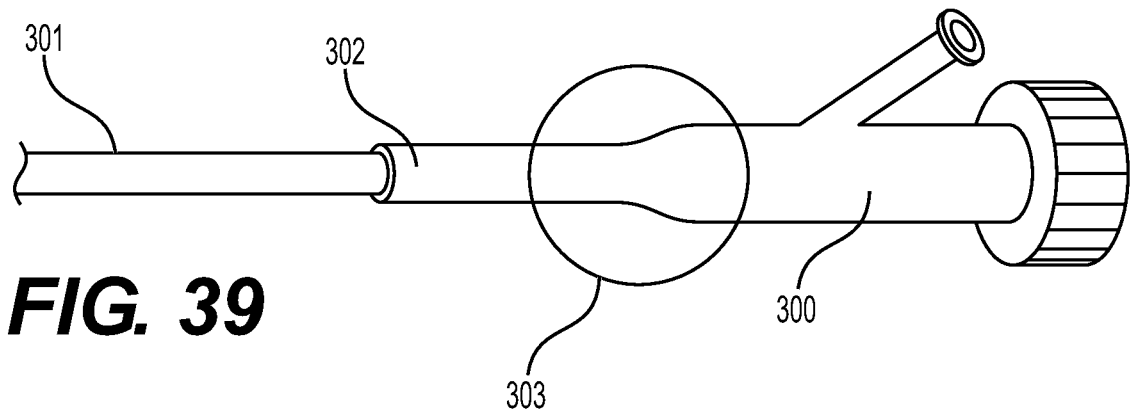
Figure 40:
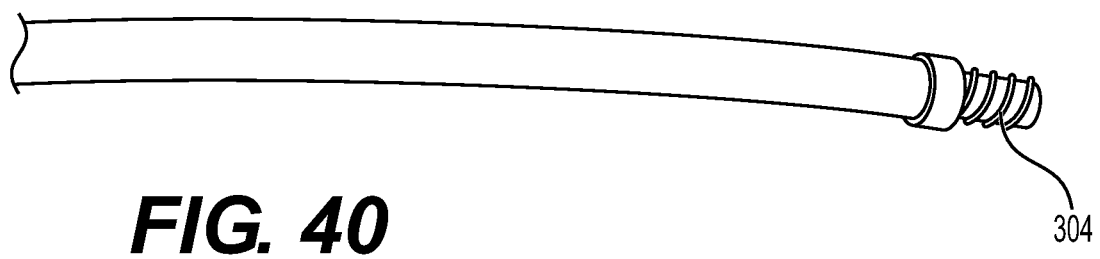
Figure 41:
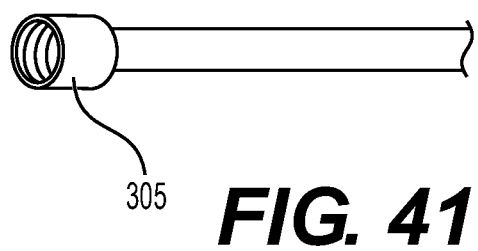

FIG. 39 shows the microcatheter hub 300 assembled with the microcatheter shaft 301. FIG. 40 shows the microcatheter shaft after detachment and FIG. 41 shows the mating end of the extendable shaft 305. By connecting the extendable shaft 305 to the microcatheter shaft 301 the working length of the catheter is increased to facilitate forwarding an intermediate or access catheter over the microcatheter while maintaining positional control. The extendable shaft 305 can then be removed and the detachable hub reconnected to the microcatheter.

Figure 42:
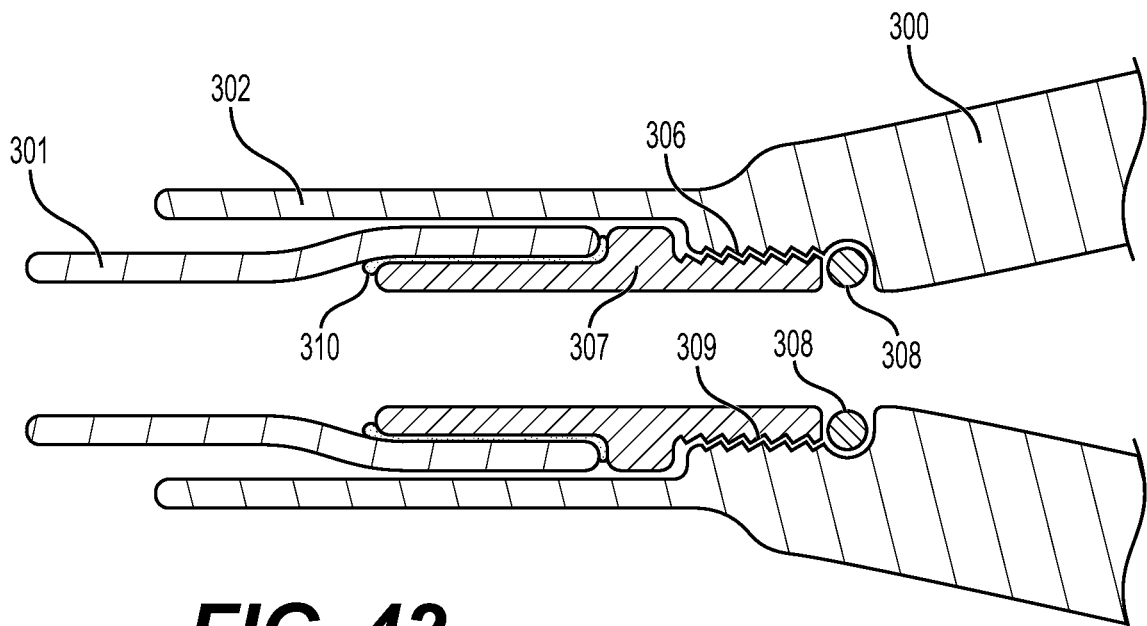

FIG. 42 illustrates the construction of the microcatheter connector 307 and detachable hub 300. The detachable hub 300 can be screwed onto the microcatheter connector 307 due to thread 309 on the connector and the mating thread 306 on the hub. 'O' ring 308 prevents any blood loss or air ingress between the connector 307 and the hub 300 when tightened.

Figure 43:
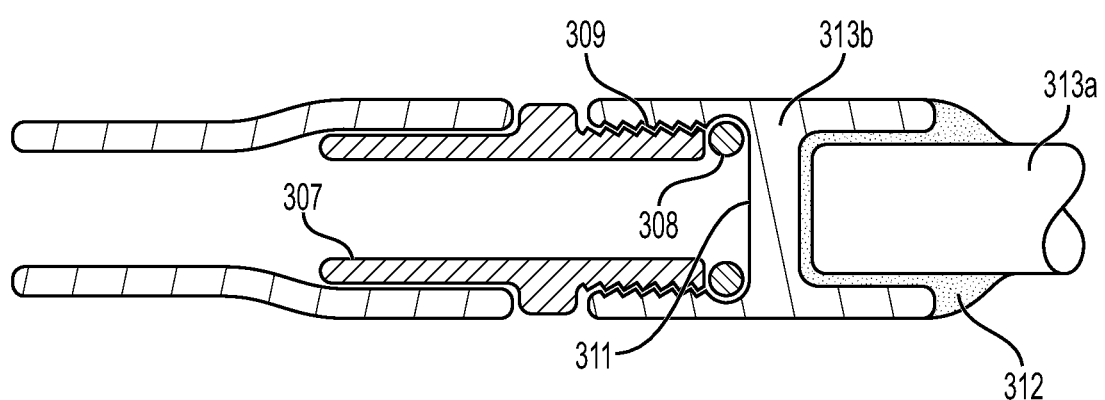

FIG. 43 shows a section view of an embodiment of the extendable shaft 305 which utilises an extension wire 313*a* and extension wire hub 313*b*. The extension wire 313*a* and hub 313*b* are shown screwed onto the microcatheter shaft 301 and connector 307.

FIGS. 44 to 46 show another embodiment of a detachable hub where the microcatheter shaft 301 is connected to the detachable hub 317 by a compressible 'O' ring 316. The 'O' ring 316 sits in a groove on the moulded hub 320 which is connected to the microcatheter shaft 301. The 'O' ring is compressed by rotating part of the housing 321 on the detachable hub 317. The extension tube 318 can be pushed over the moulded hub 320 on the microcatheter shaft 301 after the hub 317 has been removed. The extension tube 318 is then held in position by the spring clip 319 engaging with the groove on the moulded hub 320.

FIGS. 47 to 50 illustrate a method of manufacture of a large diameter aspiration catheter. The aspiration catheter is highly trackable so that it can be navigated to tortuous/distal cerebrovascular location.

Figure 47:
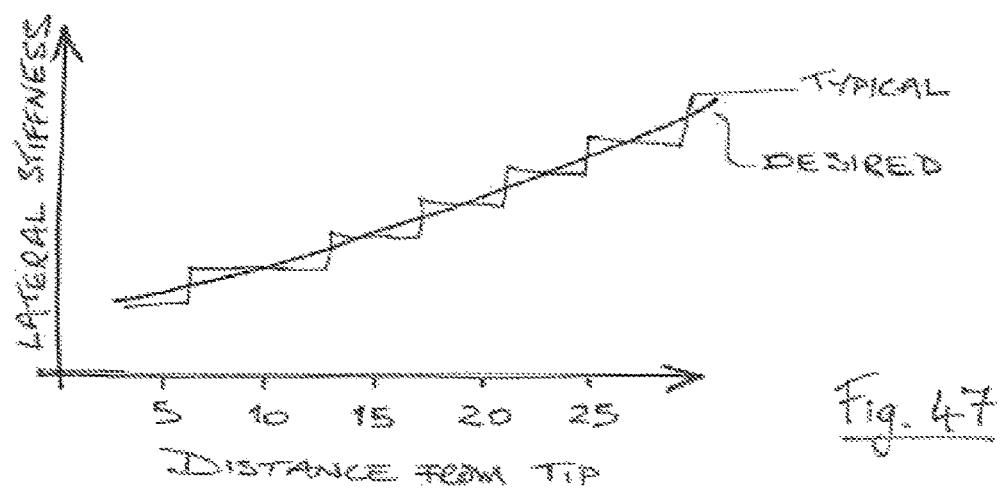
FIGS. 47 to 51 illustrate the creation of the distal segment with a continuous and smooth stiffness profile.

FIG. 47 is a graph of lateral stiffness with distance from the tip.

Figure 48:
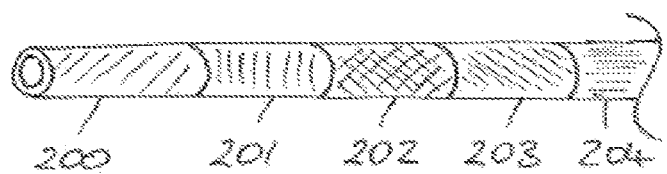

FIG. 48 illustrated a conventional diagram in which different tubular segments 200, 201, 202, 203, 204 are of different materials. The segments are used to create a stepped material stiffness profile (gradually increasing modulus/share hardness).

Figure 49:
Figure 50:
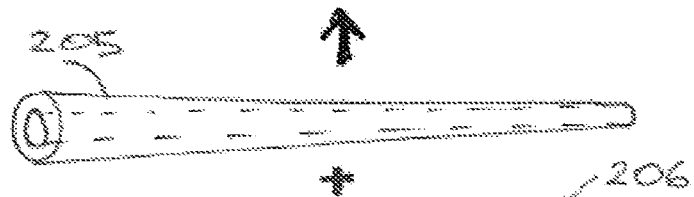
Figure 51:
Figure 56:
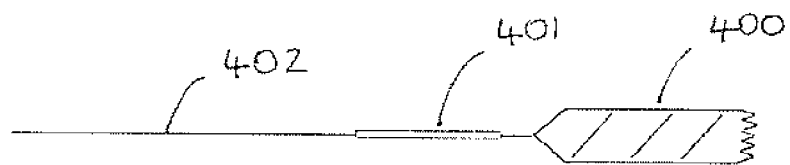
FIGS. 56 to 59 illustrate a clot receptor device and system according to the invention.
Figure 57:
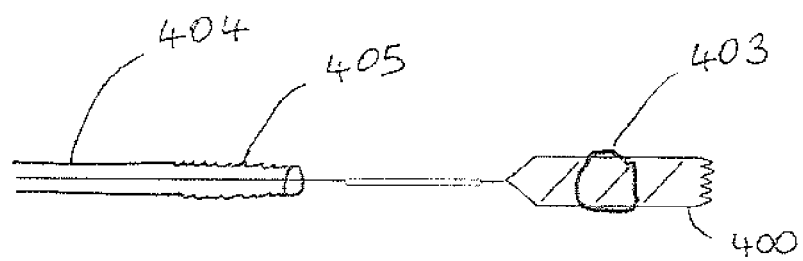
Figure 58:
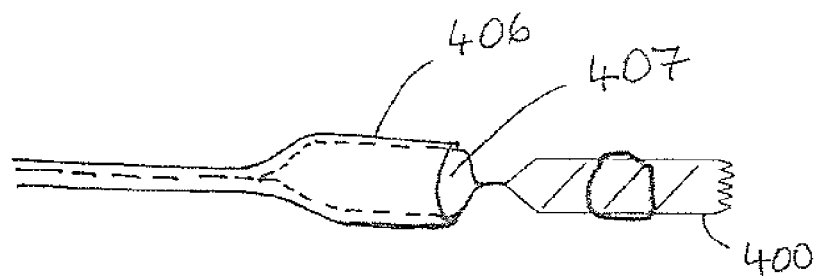
Figure 59:
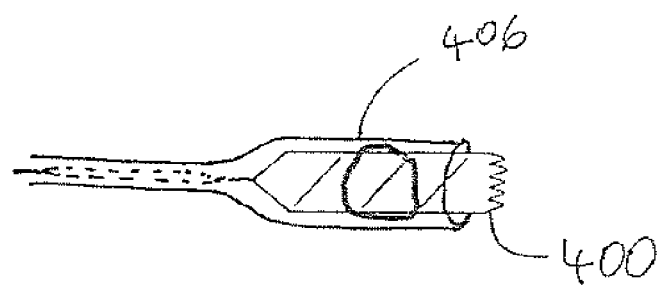

FIG. 49 illustrates a distal segment according to the invention in which a smooth stiffness profile is created by blending elements 205, 206 of different modulus. For example, tapered tubes 205, 206 (FIGS. 50, 51) may be placed on a mandrel overlapping each other and use heat to cause them to melt and flow into each other. The resultant tube may then be applied to a threaded or spiral wire or unreinforced base, or use as a stand-alone catheter.

Referring to FIGS. 52 to 55 there is illustrated a dual lumen aspiration catheter to aid with aspiration and prevent the lumen of the catheter getting blocked with clot.

Lumen A—a smaller diameter lumen can be used to retrieve the device into and cause the clot to shear off. The distal end of Lumen A could be flush with or recessed from the distal tip of Lumen B.

Lumen B—the larger lumen would have aspiration constantly applied to it, to aspirate the clot that is sheared off the device when it is retrieved into the smaller lumen (Lumen A).

The smaller lumen A may have an inner diameter to facilitate the introduction of a microcatheter through the lumen. The microcatheter can then be inserted through this lumen and across the clot as per standard procedure. The stentriever device can then be deployed across the clot. Retrieving the stentriever and clot into the catheter causes the clot to be sheared off the stentriever within the aspiration catheter. This configuration prevents the clot snagging on the struts of the stentriever device and blocking the aspiration lumen. The larger diameter lumen may have a diameter of about 0.058 inch and may have aspiration applied to it to aspirate the clot as the device is being retrieved into the smaller diameter lumen.

One clot receptor catheter tip according to the invention the clot receptor tip is expanded by means of a balloon, which may be attached to the shaft of a thrombectomy device, or to a microcatheter, or may be integral to the clot receptor catheter itself One embodiment of such a device is shown in these FIGS. 56 to 59. The device comprises a thrombectomy device 400 with an inflation lumen 402 extending from the proximal end of the shaft to a balloon 401 at the distal end of the shaft, and an clot receptor catheter 404 with a flexible expandable distal section 405. The thrombectomy device 400 is expanded in the clot 403. Either the thrombectomy device and clot are then retrieved towards the clot receptor catheter 404 or the clot receptor catheter is advanced towards the thrombectomy device. The balloon 401 at the distal end of the device is positioned so that the distal end is in line with the distal end of an intermediate catheter. The balloon is expanded to plastically deform 406 the distal end of the clot receptor catheter and then deflated. The resultant open mouth 407 of the clot receptor catheter allows the entire device and clot to be retrieved into the intermediate catheter. This prevents loss of clot on retrieval into a small lumen of a conventional intermediate catheter. The expansile distal portion 405 of the clot receptor catheter may be formed of a polymeric material with a low modulus and a high elongation strain to break of greater than 100%, and ideally greater than 300%. It may also comprise a support structure of a metallic material such as stainless steel which can be plastically deformed by the balloon and can then retain its deformed shape with sufficient integrity to accept the thrombectomy device and clot.

The balloon expandable tip of the invention can be applied to any catheter—standard or rapid exchange, and can be used with or without a thrombectomy device to aid in the aspiration and/or retrieval of clot from blood vessels.

Figure 60:
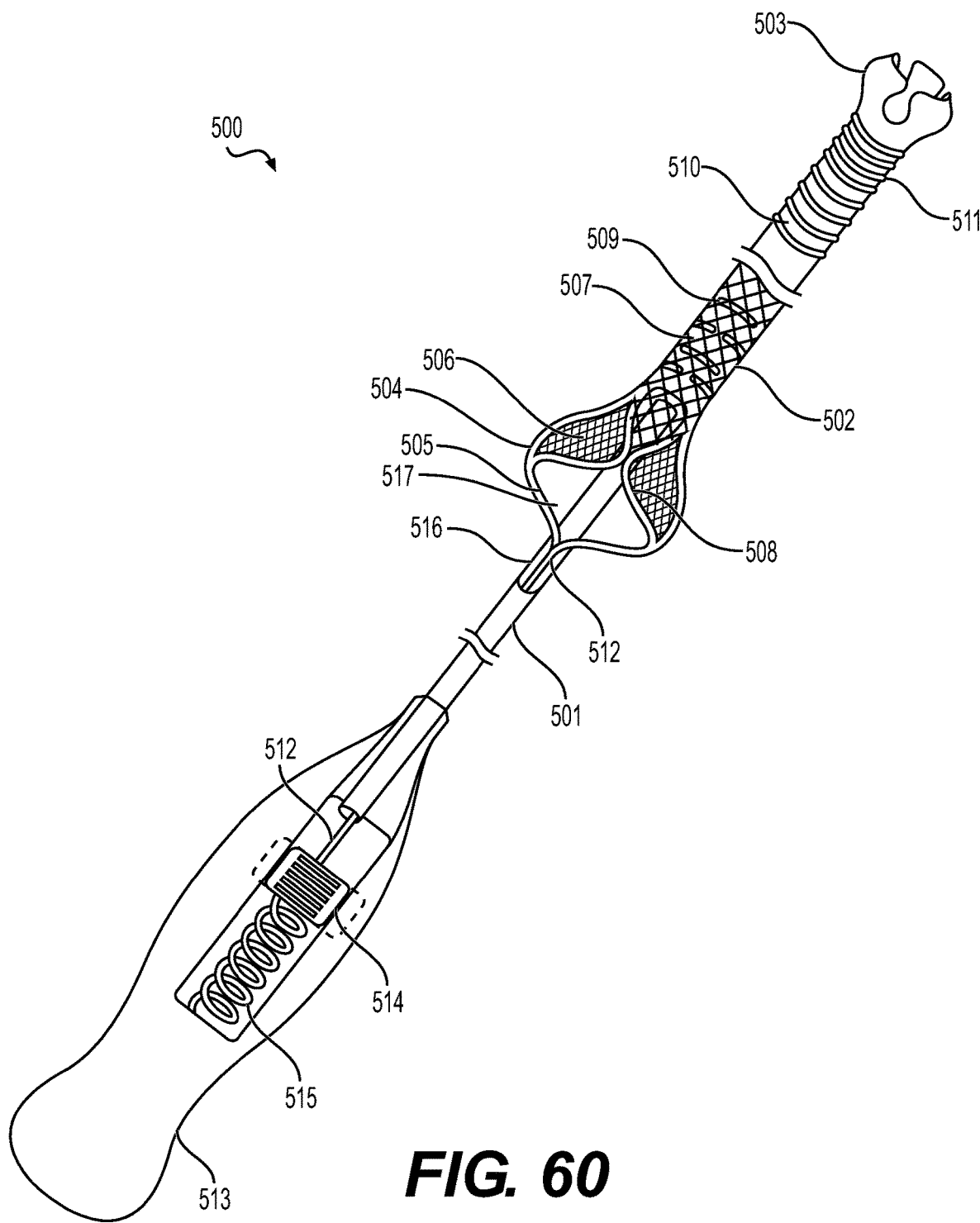
FIG. 60 illustrates a clot receptor device according to the invention.

FIG. 60 illustrates an RX clot removal catheter 500. This device 500 is very similar in design and in use to that shown in FIGS. 11a-d, except that the element 504 is an actuatable flow restrictor or seal, which can be selectively engaged or disengaged by the operator. The catheter 500 comprises a proximal elongate shaft 501 and a distal generally tubular portion 502. The distal portion 502 comprises reinforcement member 507 and a polymeric cover member 510, and extends from an entry/exit port 517 to a distal clot reception tip 503. The cover member 510 may comprise multiple layers and segments. A low friction inner layer may be employed as a lining for the lumen of the tubular section, a highly compliant membrane 506 may be employed to cover the actuatable flow restrictor/seal region, and a low modulus polymer may be employed to cover the main tubular body.

The distal end or tip 503 may comprise any of the designs shown elsewhere in this document. In a preferred embodiment the tip 503 is connected to the distal end of the tubular portion 502 by a hinge element 511. This hinge element may simply be a short region of the tubular section configured to have a high degree of lateral flexibility relative to the rest of the tubular section. This flexibility may be achieved by having a short region of the tubular section without any reinforcement element 507, or alternatively the reinforcement at that region could be a highly flexible reinforcement such as a generally spiral metallic coil.

The actuatable flow restrictor or seal 504 comprises a framework 508, with a membrane covering 506. The framework 508 is at least partially collapsible by retraction of actuation member 512, which runs through proximal elongate shaft 501 and is connected at its proximal end to slider element 514, which is in turn slidably constrained within handle 513, and coupled to spring element 515. Proximal elongate shaft 501 may comprise a tube of stainless steel, Nitinol or other metallic or high modulus polymeric material, and may contain a liner in order to provide a low friction internal surface against which the actuation member 512 may slide. The shaft 501 may be tapered or may be slotted in order to provide a smooth transition in stiffness over its length. In the embodiment shown a portion of the shaft material has been removed from the distal portion 516 of shaft 501 in order to provide an exit port for actuation member 512 and to provide a connection member to the proximal end of tubular portion 502. This distal portion 516 may also be flattened, which may assist in creating a similar curvature to that of the tubular portion 502 so that the two portions can be smoothly joined together by welding, soldering, bonding or other appropriate method of fixation. The main body of the shaft may also have an oval or somewhat flattened profile, as this may be beneficial in allowing the user to seal a haemostasis valve around the shaft and a microcatheter when the two are side by side in the guide/sheath as shown previously in FIG. 11a.

The reinforcement member 507 may be formed from a metal (such as stainless steel or Nitinol or MP35N or other suitable alloy) or from a high modulus polymer material. In one embodiment (as shown) the reinforcement is formed from a tube from which sections 509 have been cut away to add lateral flexibility while maintaining column and hoop strength.

In the catheter illustrated in FIG. 60 the actuatable seal 504 is located adjacent to the proximal end of the distal tubular section, where it also forms the exit/entry port to the proximal end of the distal tubular section 502, but it could be positioned more distally in other variants of the invention. Once the catheter has been advanced to a position proximal of or adjacent the target clot the seal can be actuated to effect a seal between the proximal portion of the tubular section of the RX clot removal catheter and the inner lumen of the guide catheter. A vacuum force can then be applied to the proximal end of the guide catheter using a syringe or pump. This vacuum force will create a low pressure region inside the guide catheter which will extend (via the seal) into the distal tubular portion of the RX clot removal catheter. This low pressure will create a pressure gradient at the tip of RX clot removal catheter which will encourage the flow of clot into the catheter.

In some scenarios, such as when retrieving a firm clot with a high fibrin content, it may not be possible to aspirate the clot fully into and through the RX clot removal catheter, and the clot may become lodged at the tip of the catheter. In such a case it may be necessary to remove the RX clot removal catheter with the clot through the guide catheter and out of the patient. It may be desirable to create reverse flow in the cerebral vasculature during this retrieval process in order to prevent the escape and distal migration of any fragments of the clot being retrieved. This can be done by disengaging the RX clot removal catheter seal so that the low pressure zone is redirected into the distal lumen of the guide catheter. Thus pressure gradient between the blood in the cerebral vasculature and the fluid within the guide catheter lumen causes a flow of the blood from the high pressure region to the low pressure region. The seal as shown can also serve to create a guiding feature to assist the advancement of another device into the tubular distal section of the clot removal catheter. This might be advantageous if for example the catheter was used as a primary clot debulking tool—so that it was advanced to a target clot and aspiration was applied to it through the guide catheter to remove the occlusive clot but was not successful in removing all of the clot. In this case a microcatheter (and guidewire if desired) could be advanced through the RX clot removal catheter and across the remaining clot so that a thrombectomy device could then be advanced through the microcatheter. The thrombectomy device and remaining clot could then be withdrawn into the RX clot removal catheter (under aspiration if desired) to complete the recanalisation of the patient's vessel.

Figure 61A:
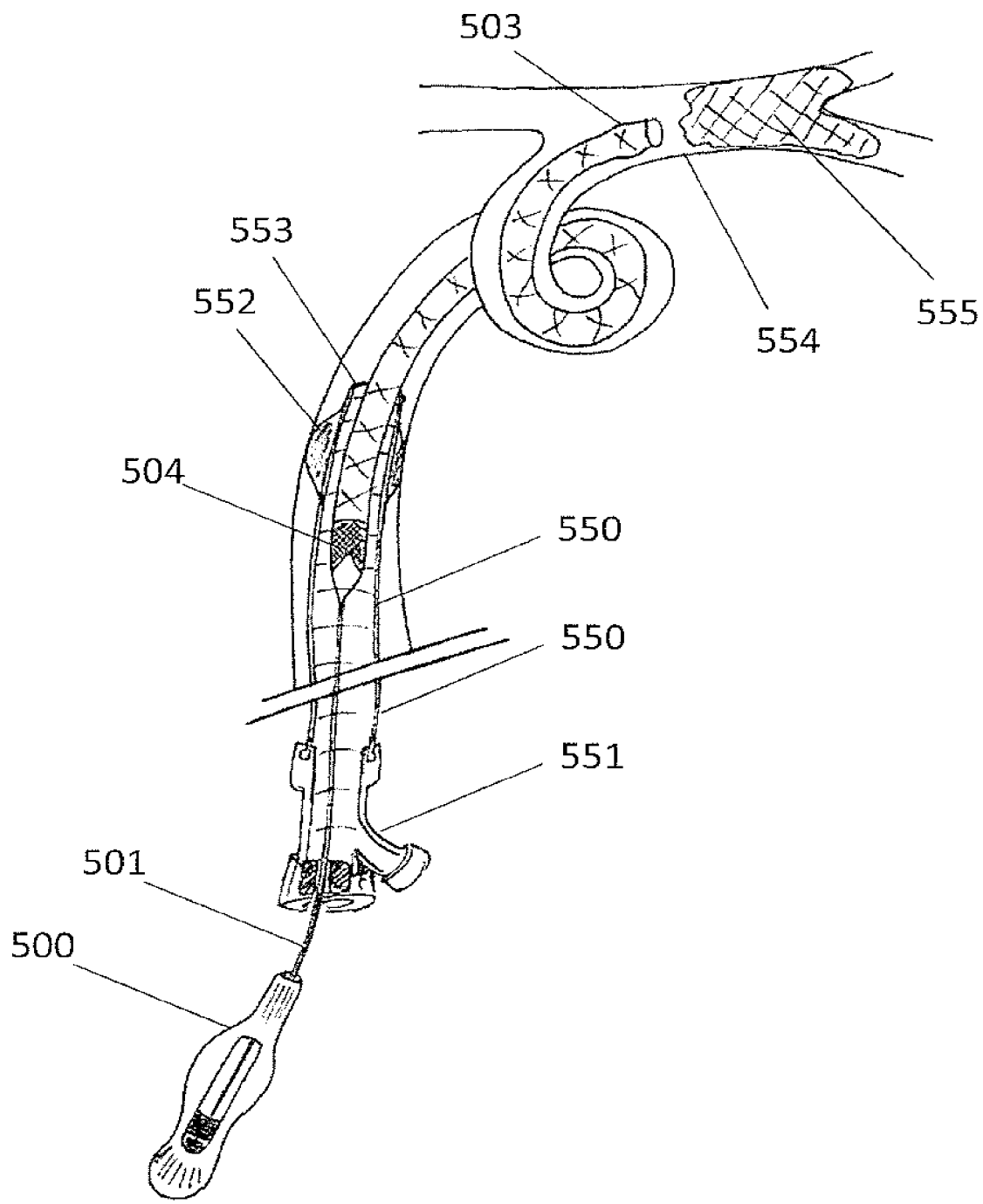
FIGS. 61a-c illustrate a clot receptor device and system according to the invention.
Figure 61B:
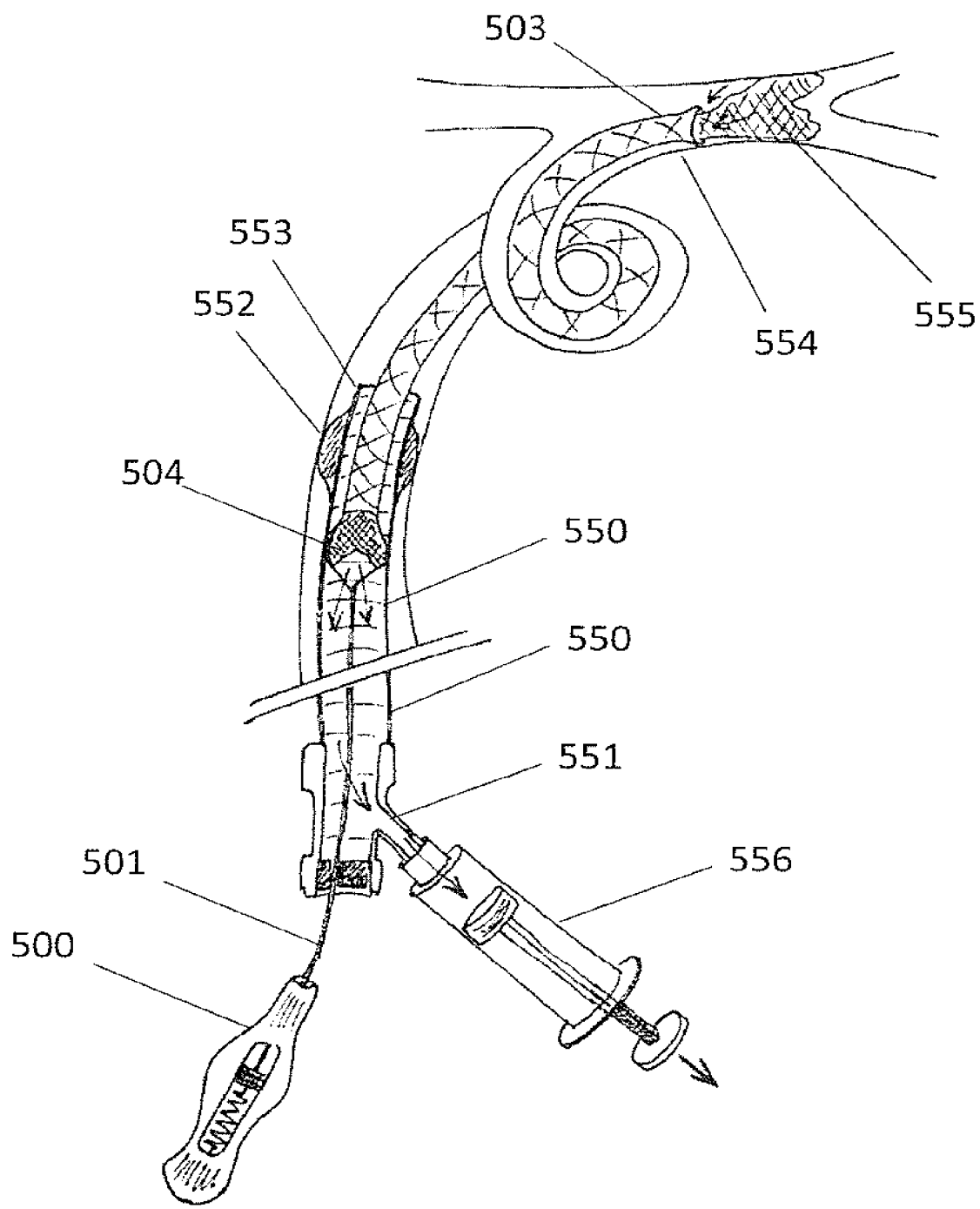
Figure 61C:
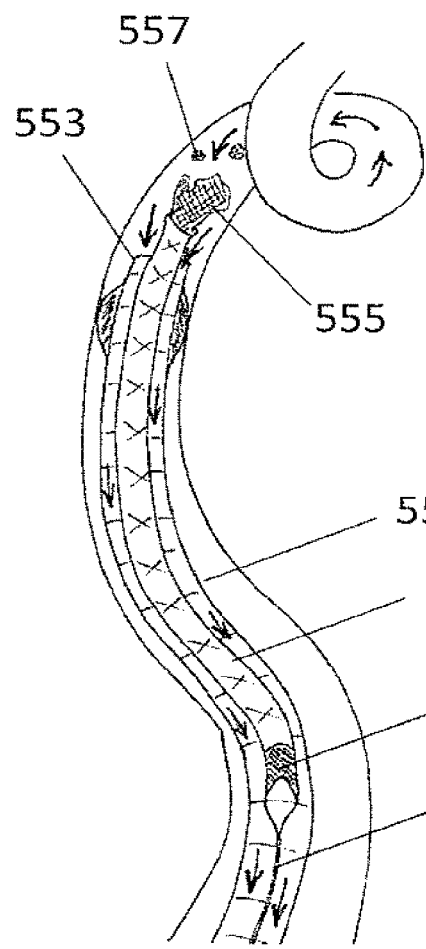

FIGS. 61a-61c illustrate a method of use of the RX clot removal catheter 500. This catheter can be used in a similar manner and for a similar purpose to catheter 101 illustrated previously in FIGS. 10 and 11, except that the seal/flow restrictor of catheter 500 can be selectively activated or deactivated by the user. The catheter can be used as the primary clot retrieval device as shown in FIGS. 61a-c, or as an adjunctive device as shown in FIGS. 11a-d. FIG. 61a shows the catheter 500 advanced through a guide catheter 550 towards a target clot 555 located in blood vessel 554. In this case the catheter 550 has an external flow restrictor in the form of a balloon at its distal end.

The method of use of such a system could entail: Accessing the patient's vasculature using standard methods, advancing a guiding catheter or sheath 550 to a region proximal of the target occlusive clot 555, advancing the RX clot removal catheter 500 through the guide/sheath to a location proximal or adjacent to or within the target clot as shown in FIG. 61a (which may be achieved with the aid of a microcatheter and/or guidewire and/or thrombectomy device), activating the proximal flow restrictor/seal 504 of the catheter 500 to connect the lumens of the two catheters, inflating the external balloon (if present and if desired) at the end of the guide/sheath, aspirating using a syringe 556 or vacuum pump (not shown) through the a connector 551 attached to the proximal end of the guide/sheath 550 so that a pressure gradient is created which sucks blood and clot into the mouth 503 of the Rx clot removal catheter 500 and through the catheter 500 and the guide/sheath 550 and into the syringe as shown in FIG. 61b. If any clot remains caught in the end of the catheter tip 503 (as may happen if the clot has a significant organized fibrin component such as may occur in clots originating from a heart valve or an atrial appendage for example) it may be necessary to withdraw the catheter 500 and the trapped clot 555 together through guide/sheath 550 and out of the patient as shown in FIG. 61c. In such a scenario the flow restrictor/seal 504 may be de-activated so as to enable a vacuum force applied by the syringe to the guide/sheath to be transmitted to the distal end 553 of the guide/sheath and thus create flow reversal and draw blood and any clot fragments 557 back into the tip of the guide/sheath as the captured clot is retracted.

Figure 62:
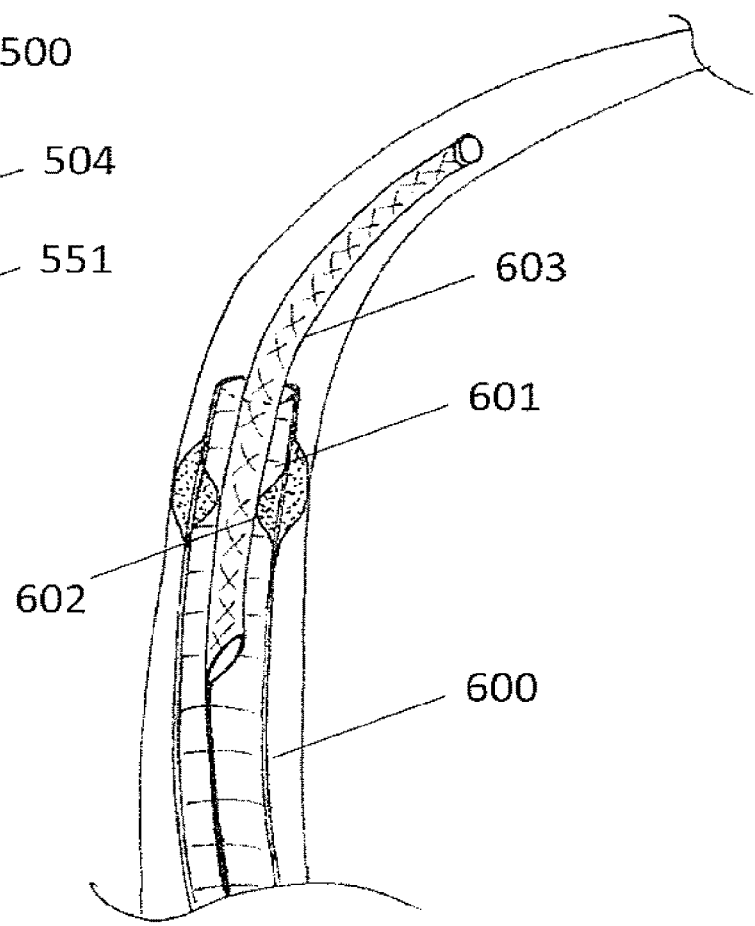
FIG. 62 illustrates a portion of a clot receptor device and system according to the invention.

FIG. 62 depicts another system of this invention which functions in a similar manner to the previously described Rx catheter systems, but in this case the flow restrictor or seal between the inside of the guide/sheath 600 and the outside of the Rx catheter 603 is created by a sealing element 602 attached to the inside of the guide/sheath 600. This sealing element 602 may comprise an inflatable balloon, similar to the external flow restricting balloon 601 shown on the outside of the guide/sheath.

Figure 63:
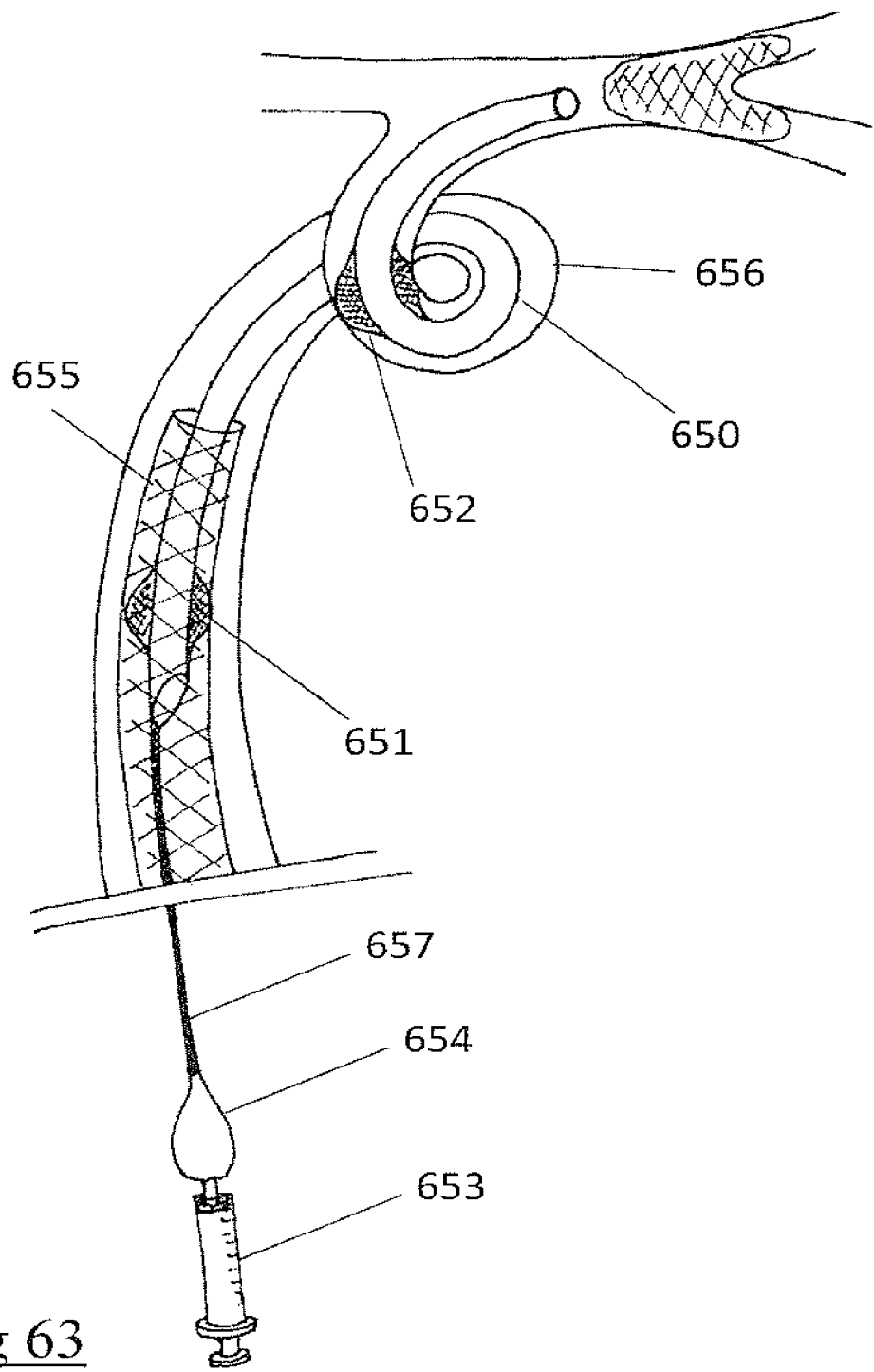
FIG. 63 illustrates a clot receptor device according to the invention.

FIG. 63 depicts another system of this invention in which an Rx clot retrieval catheter 650 has two flow restrictor/seal elements 651 and 652. The more proximal restrictor 651 is used to restrict flow between the Rx catheter 650 and the guide catheter 655 within which it is positioned, while the more distal restrictor 652 is used to create a flow restriction within vessel 656. The combination of these two flow restrictors means that a vacuum or negative pressure can be applied to the proximal end of guide catheter 655 and transmitted to the distal end of Rx catheter 650 in such a way that any blood aspirated into the mouth of Rx catheter 650 is not supplied from the body of blood proximal to seal 652 in vessel 656.

This system enables a physician to use a standard guide or sheath to rapidly create an access path to the region of the target occlusion, and then use the Rx catheter 650 to quickly access and aspirate the target clot from the vessel. This system provides a major advantage in the speed and ease with which a physician will be able to access and retrieve the clot. The provision of the distal vessel seal 652 on the Rx catheter rather than on the guide or sheath means that this seal can be placed more distally in the vasculature, past the petris portion of the carotid vasculature when used in the ICA for example, which means less likelihood of vessel collapse when a suction force is applied, and less likelihood of vessel spasm.

In a preferred embodiment the flow restrictors/seals are actuatable and are formed from compliant balloons, which are inflated via a hollow shaft 657 by means of a syringe or inflator 653 applied to handle 654 of the Rx catheter 650. In other embodiments the proximal flow restrictor may be passive (i.e. it cannot be selectively activated or inactivated) as shown in several other designs in this disclosure. In yet other embodiments the distal seal may be actuated by means of an actuating member rather than an inflation lumen.

Most of the Rx (rapid exchange) catheters disclosed herein share some common features and geometry. Taking catheter 500 of FIG. 60 as an example: They have a distal generally tubular portion 502 comprising an inner lumen which starts with an opening or entry/exit port 517 and ends in a distal tip or mouth 503 into which clot is received. They have a proximal elongate shaft 501 which is connected at its distal end to the entry/exit port 517 and at its proximal end in some embodiments to a handle 513. The preferred geometry of these catheters depends on the target clot location. For clots located in the anterior or posterior cerebral anatomy the distal tubular portion 502 is preferably greater than 10 cm (so that it can extend from within the distal end of a guide/sheath which may be located in an internal carotid artery or a vertebral artery, right up to the proximal face of a target clot), and less than 40 cm so that the minimum possible length of tubular portion 502 is located within the lumen of the guide/sheath, thus maximising the internal volume of the combined guide/Rx catheter system for optimum aspiration efficacy).

The optimal internal and external diameters of the Rx catheter depends very much on the site of the target clot and the size of the guide catheter or sheath through which the catheter is to be advanced. In the case of retrieval of occlusive clots from cerebral vessels the likely vessel diameters range from approximately 1.5 mm up to 6 mm, with 3 mm being a very typical diameter. Guide catheters/sheaths used in these scenarios have typically an internal diameter of between 0.060" and 0.095", so that a suitable system might consist of a guide catheter with an internal diameter of 0.078" and an Rx clot retrieval catheter whose distal tubular section has an outside diameter of 0.070" and an inside diameter of 0.062". Such a system provides a very significant benefit in terms of flow resistance over an equivalently sized conventional combination of a guide and intermediate/ aspiration (not rapid exchange) catheter. In particular the effective proximal lumen of the system of this invention is that of the guide catheter (0.078"), while the effective proximal lumen of the conventional system would be that of the intermediate/aspiration catheter (0.062"). This results in a significantly lower flow restriction in the Rx system of the invention, which means that for a given vacuum/suction force applied to the proximal end of the system, a much greater flow will be created through the system of this invention. While a conventional (not rapid exchange) intermediate/aspiration catheter may be stepped in diameter to maximise its proximal internal diameter, this proximal internal diameter must always be significantly smaller than the guide/sheath in which it is positioned. This is not the case in the system of this invention.

Yet another embodiment of this invention is shown in FIGS. 64a-d, which depict a distal end configuration which could be employed with any of the clot retrieval catheters previously shown. The catheter distal end 700 has an integrated control member 701, which forms a loop 704 at the tip where it is connected to tip members 703 so that it acts like a draw string when pulled. The tip may comprise relatively stiff members 703 interspersed with relatively compliant members 702, so that the tip has both axial stiffness (to permit effective operation of the drawstring mechanism) and radial compliance (to allow expansion and contraction of the tip).

Figure 64A:
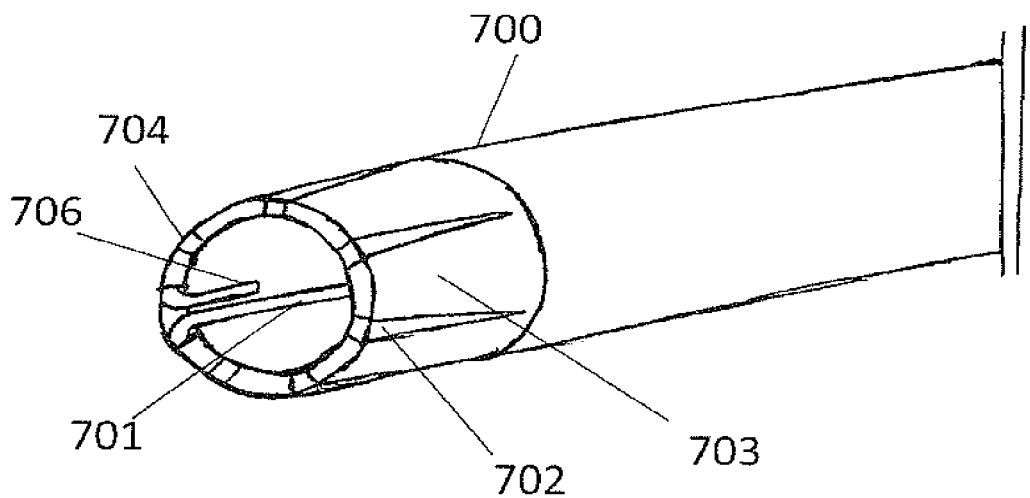
FIGS. 64a-d illustrate an expansile tip of a clot collector device of the invention and
FIG. 65 illustrates a rapid exchange aspiration catheter according to the invention.
Figure 64B:
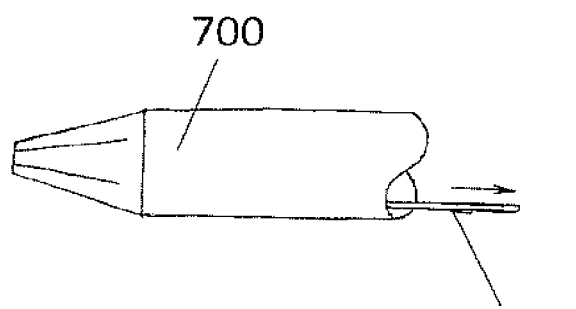

Therefore when actuated by pulling as shown in FIG. 64b, the control member causes the tip of the catheter to reduce in diameter. This can improve the ability of the catheter to track through tortuosity and across obstacles such as the origin of the ophthalmic artery.

Figure 64C:
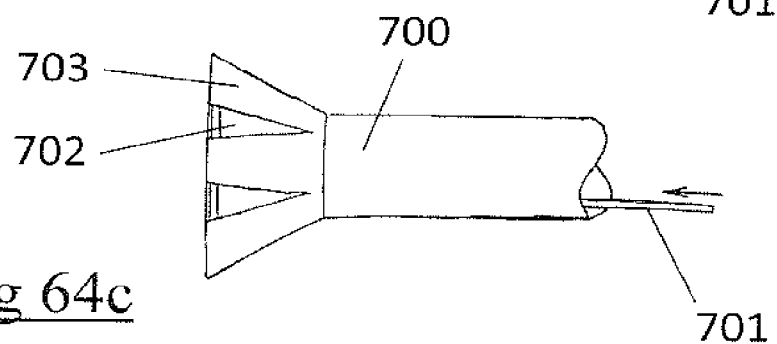

Similarly when the control member is pushed forward it can cause or allow the catheter tip to expand forming a funnel shape as shown in FIG. 64c. This can improve the ability of the catheter to aspirate clots and also act as a flow restrictor in the vessel.

In use the control member may be pulled back during insertion of the catheter to improve accessibility. It can then be forwarded to increase the diameter of the tip and aspirate the occlusion.

Figure 64D:
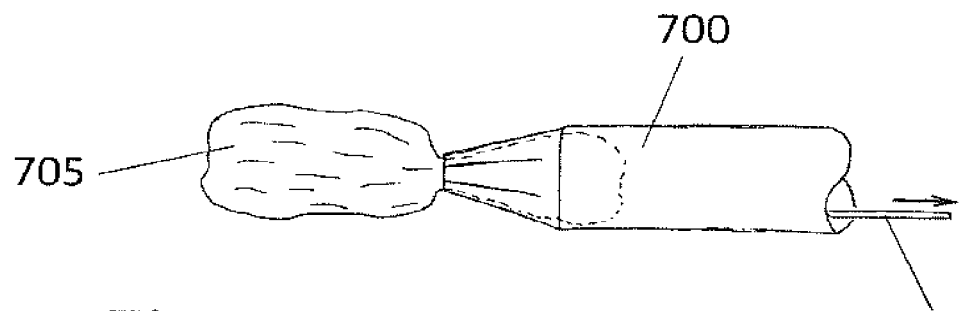

If the occlusion or blood clot can only be partially aspirated, then the tip diameter can be reduced again by pulling the control member, causing the clot to be trapped as shown in FIG. 64d, reducing the risk of the clot travelling to a new territory during retraction of the catheter and improving dislodgement.

The flaps 703 of the catheter tip are not rigidly connected to the integrated control member 701 but form a loop which can slide over the control member. The control member distal end 706 may also be fixed to the inner surface of the catheter.

Figure 65:
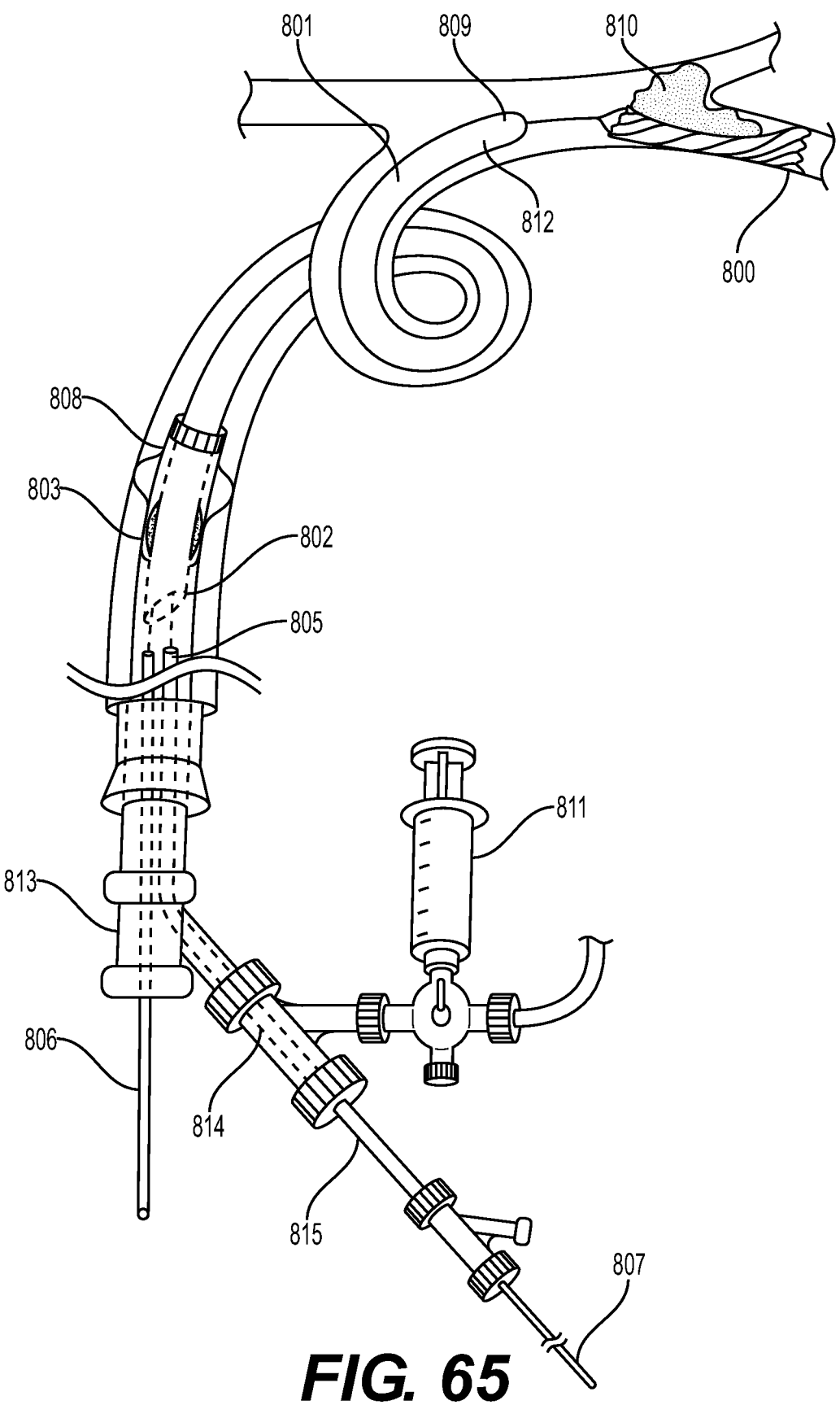

Referring to FIG. 65 there is illustrated an aspiration catheter 801 according to this invention in use in a thrombectomy procedure. The catheter 801 is similar to catheter 101 of FIGS. 10 and 11 and provides a proximal seal 802 against a guide catheter inner lumen 803 so that aspiration applied by syringe 811 (or a pump or by other means) through guide catheter 808 (via a rotating haemostasis valve (RHV) 814) can be transferred through to the distal end 812 of the aspiration catheter. Thrombectomy device 800 is shown deployed within clot 810, having been delivered through microcatheter 809 by means of proximal shaft 807. The method of use of the system illustrated is very similar to that described in FIGS. 11a-d, except that in this embodiment the proximal end 815 of the microcatheter 809 and proximal end 806 of Rx aspiration catheter 801 are positioned within separate branches of a rotating hemostasis valve (RHV) 813. This configuration provides significant ease of use advantages over the configuration described in FIG. 11. In particular the RHV 813 can be more easily sealed around the proximal shaft 806 of the aspiration catheter to prevent any air ingress (or fluid leakage) during aspiration. In addition the user has better control over the aspiration catheter 801, microcatheter 809 and thrombectomy device 800 relative to the guide catheter 808, and can use RHVs 813 and 814 to lock and hold the aspiration catheter or microcatheter independently of each other.

One embodiment of the method of use of such a system could consist of the following steps: Accessing an arterial blood vessel of a patient using conventional means such as an introducer and guide catheter 808 and/or sheath, advancing Rx aspiration catheter 801 through a first branch of RHV 813 attached to proximal end of guide catheter 808, advancing a microcatheter 809 through a second branch of RHV 813 and through the aspiration catheter 801 and guide catheter 808 up to and across a target occlusive clot 810 with or without the aid of a guidewire, removing the guidewire (if used) and advancing a mechanical thrombectomy device 800 such as a stent-retriever through the microcatheter 809 to the target clot 810, retracting the microcatheter 809 at least a few cm to deploy a mechanical thrombectomy device 800 within the clot 810, advancing the aspiration catheter 801 up to a position just proximal of the clot 810 (or within the clot, or considerably proximal of the clot if vessel disease or tortuosity makes access difficult), optionally creating flow arrest by inflating the balloon of the guide catheter 808 (if used, or by other means), aspirating through the aspiration catheter 801 using a syringe 811 or pump connected to the guide catheter 808 while withdrawing the mechanical thrombectomy device 800 towards and into the distal mouth 812 of the aspiration catheter 801, withdrawing the clot 810, mechanical thrombectomy device 800 and microcatheter 809 through the aspiration catheter 801 and guide catheter 808 and out of the patient while continuing to aspirate.

A possible variant of the final step of the above method could involve removing the aspiration catheter along with the clot 810, mechanical thrombectomy device 800 and microcatheter 809. This variant is useful if a large and/or firm clot is encountered which the physician cannot (or does not wish to) fully withdraw into the mouth of the aspiration catheter. In such a situation the RHV 813 must be removed once the exit port 805 of the aspiration catheter 801 reaches the RHV 813.

Another method of use of such an Rx aspiration catheter system is to retrieve clot using aspiration without the use of a thrombectomy device. The rapid exchange shaft of this invention provides great advantages in terms of speed, deliverability, ease of use and aspiration lumen. A microcatheter or other similar catheter and guidewire may be used to provide support to assist in tracking the aspiration catheter to the target site in a similar manner to that illustrated in either FIG. 65 or FIGS. 11*a-d*.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

What is claimed is:

1. A system for assisting in the retrieval of a clot from a vessel, the system comprising:
   an outer catheter;
   an inner catheter disposed in a lumen of the outer catheter, the inner catheter comprising:
   a distal end;
   a proximal end;
   a distal segment;
   a proximal segment; and
   a lumen extending proximal of the distal end and terminating at a transfer port at the proximal end of the distal segment;
   a seal located on the outer surface of the inner catheter distal of the transfer port, the seal capable of sealing against the lumen of the outer catheter so that aspiration applied through the outer catheter is configured to be transferred to the inner catheter; and
   a first rotating hemostasis valve (RHV) through which aspiration is applied, wherein the outer catheter and the inner catheter are each disposed inside the RHV; and
   wherein the first RHV is configured to seal around a proximal shaft of the inner catheter thereby preventing any fluid ingress or leakage during aspiration.

2. The system of claim 1, further comprising: an actuator for selectively engaging and/or disengaging the seal.

3. The system of claim 1, wherein the seal comprises a framework and a membrane coupled to the framework, the framework being movable between an expanded configuration and a retracted configuration, wherein the distal end of the inner catheter comprises a mouth for reception of clot.

4. The system of claim 3, wherein the mouth is defined by an expansile tip comprising an elastic sleeve having a high elastic strain limit and a low modulus of elasticity to permit expansion by a low radial force, the sleeve being expandable in the deployed configuration to define an enlarged distal tip for reception of clot.

5. The system of claim 3, wherein the mouth is defined by an expansile tip comprising a diameter at least about 50% larger than a central diameter of the inner catheter.

6. The system of claim 3, wherein the distal segment includes a hinge adjacent to the mouth.

7. The system of claim 1, wherein the seal seals the lumen between an outer surface of the inner catheter and an inner surface of the lumen of the outer catheter thereby preventing backflow of blood into a distal tip of the outer catheter.

8. The system of claim 1, wherein the seal is located on an inside surface of the outer catheter.

9. The system of claim 1, wherein the seal allows for suction out from a distal end of the outer catheter, and wherein the seal is positioned between the outer catheter and an outer surface of the inner catheter.

10. The system of claim 1, wherein the seal is located against an inner surface of the lumen of the outer catheter so that aspiration applied by a syringe or a pump through outer catheter is transferrable through to the distal end of the inner catheter.

11. The system of Claim 1, further comprising:
   a second RHV configured to house a first portion of a proximal end of the microcatheter,
   wherein the first RHV comprises a first branch and a second branch, the first branch comprises the proximal end of the inner catheter and the second branch comprises second portion of the microcatheter distal to the first portion.

* * * * *